(12) United States Patent
Harrington et al.

(10) Patent No.: US 11,179,129 B2
(45) Date of Patent: Nov. 23, 2021

(54) SYSTEMS AND METHODS FOR PLANNING AND EXECUTING AUTOMATED MULTI-AXIS MOTION IN TREATMENT

(71) Applicant: VARIAN MEDICAL SYSTEMS, INC., Palo Alto, CA (US)

(72) Inventors: Adam Scott Harrington, Glastonbury, CT (US); William Kearns, Clemmons, NC (US); Joakim Olavi Pyyry, Helsinki (FI); Janne I. Nord, Espoo (FI); Agam Sharda, Fremont, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 996 days.

(21) Appl. No.: 15/379,411

(22) Filed: Dec. 14, 2016

(65) Prior Publication Data

US 2018/0160994 A1    Jun. 14, 2018

(51) Int. Cl.
| | |
|---|---|
| *A61B 6/00* | (2006.01) |
| *A61N 5/10* | (2006.01) |
| *A61B 6/03* | (2006.01) |
| *A61B 6/04* | (2006.01) |

(52) U.S. Cl.
CPC ............ *A61B 6/5217* (2013.01); *A61B 6/032* (2013.01); *A61B 6/0487* (2020.08); *A61B 6/4417* (2013.01); *A61N 5/103* (2013.01); *A61N 5/1082* (2013.01)

(58) Field of Classification Search
CPC .... A61N 5/103; A61N 5/1082; A61N 5/1054; A61N 5/1061; A61N 5/1067; A61N 5/1069; A61N 5/107; A61N 2005/1054; A61N 2005/1061; A61B 6/0457;
(Continued)

(56) References Cited

U.S. PATENT DOCUMENTS

| | | | |
|---|---|---|---|
| 6,038,283 A | * | 3/2000 | Carol ..................... G16H 20/40 378/65 |
| 6,272,368 B1 | | 8/2001 | Alexandrescu |

(Continued)

FOREIGN PATENT DOCUMENTS

| | | |
|---|---|---|
| CN | 200984237 Y | 12/2007 |
| DE | 10 2008 046 345 B4 | 7/2010 |

(Continued)

OTHER PUBLICATIONS

International Search Report and Written Opinion dated Feb. 22, 2018 for corresponding PCT Application No. PCT/US17/66164, 10 pages.

*Primary Examiner* — Dani Fox
*Assistant Examiner* — Soorena Kefayati
(74) *Attorney, Agent, or Firm* — Vista IP Law Group, LLP

(57) ABSTRACT

An apparatus for creating a radiation treatment plan for execution by a radiation treatment machine, includes: a waypoint module configured to obtain imaging waypoint data representing imaging waypoints, the imaging waypoints at least partially defining one or more positions for obtaining images of a patient during a treatment session; a treatment trajectory module configured to obtain treatment data at least partially defining a beam-on direction; a treatment plan generator configured to create the radiation treatment plan based at least in part on the imaging waypoint data and the treatment data.

24 Claims, 16 Drawing Sheets

(58) Field of Classification Search
CPC ..... A61B 6/4417; A61B 6/032; A61B 6/0487; A61B 6/5217
See application file for complete search history.

(56) References Cited

U.S. PATENT DOCUMENTS

| | | | |
|---|---|---|---|
| 6,385,477 B1* | 5/2002 | Werner | A61N 5/103 378/4 |
| 6,393,096 B1* | 5/2002 | Carol | A61N 5/1031 378/151 |
| 6,504,899 B2 | 1/2003 | Pugachev et al. | |
| 6,735,277 B2 | 5/2004 | McNutt et al. | |
| 6,888,919 B2 | 5/2005 | Graf | |
| 7,245,698 B2 | 7/2007 | Pang et al. | |
| 7,268,358 B2 | 9/2007 | Ma et al. | |
| 7,529,339 B2 | 5/2009 | Goldman et al. | |
| 7,649,981 B2 | 1/2010 | Seppi et al. | |
| 7,773,723 B2 | 8/2010 | Nord et al. | |
| 7,835,494 B2 | 11/2010 | Nord et al. | |
| 8,175,892 B2* | 5/2012 | Kapoor | G16H 20/40 705/2 |
| 8,437,449 B2* | 5/2013 | Riley | A61N 5/1038 378/65 |
| 8,986,186 B2* | 3/2015 | Zhang | A61N 5/103 600/1 |
| 9,211,423 B2 | 12/2015 | Gross et al. | |
| 2004/0042583 A1 | 3/2004 | Wackerle et al. | |
| 2004/0068182 A1* | 4/2004 | Misra | G16H 20/40 600/427 |
| 2004/0120452 A1* | 6/2004 | Shapiro | A61N 5/1064 378/19 |
| 2004/0254448 A1* | 12/2004 | Amies | A61N 5/103 600/410 |
| 2005/0228255 A1* | 10/2005 | Saracen | A61B 6/0487 600/407 |
| 2006/0067469 A1* | 3/2006 | Dooley | A61N 5/1031 378/65 |
| 2007/0071168 A1* | 3/2007 | Allison | A61N 5/1031 378/65 |
| 2007/0086569 A1* | 4/2007 | Johnsen | A61N 5/1045 378/65 |
| 2007/0189455 A1* | 8/2007 | Allison | A61B 6/5217 378/95 |
| 2008/0009731 A1* | 1/2008 | Maschke | A61B 8/5238 600/439 |
| 2008/0187097 A1* | 8/2008 | Cheng | B25J 9/1666 378/65 |
| 2008/0242969 A1* | 10/2008 | Sayeh | A61B 6/563 600/407 |
| 2008/0292158 A1* | 11/2008 | Rietzel | G16H 50/70 382/128 |
| 2008/0298550 A1* | 12/2008 | Otto | A61B 5/0036 378/65 |
| 2009/0080603 A1* | 3/2009 | Shukla | A61N 5/1049 378/25 |
| 2009/0110238 A1* | 4/2009 | Li | A61B 5/7292 382/103 |
| 2009/0180678 A1* | 7/2009 | Kuduvalli | A61N 5/1049 382/132 |
| 2010/0020931 A1* | 1/2010 | Otto | A61N 5/1038 378/65 |
| 2010/0177870 A1* | 7/2010 | Nord | A61N 5/103 378/65 |
| 2011/0080990 A1* | 4/2011 | Filiberti | A61N 5/1049 378/4 |
| 2012/0020449 A1* | 1/2012 | Yan | A61B 6/547 378/4 |
| 2012/0035470 A1* | 2/2012 | Kuduvalli | A61N 5/10 600/427 |
| 2012/0123184 A1* | 5/2012 | Otto | A61N 5/1067 600/1 |
| 2012/0271094 A1 | 10/2012 | Fuller | |
| 2013/0083894 A1 | 4/2013 | Niebler et al. | |
| 2013/0101082 A1* | 4/2013 | Jordan | A61N 5/1037 378/19 |
| 2013/0142310 A1* | 6/2013 | Fahimian | A61N 5/103 378/65 |
| 2013/0144104 A1* | 6/2013 | Adler, Jr. | A61N 5/1081 600/1 |
| 2013/0188856 A1* | 7/2013 | Adler, Jr. | A61B 5/0036 382/132 |
| 2013/0197294 A1* | 8/2013 | Nord | A61N 5/103 600/1 |
| 2014/0070115 A1* | 3/2014 | Oster | A61B 6/4452 250/492.1 |
| 2014/0275703 A1* | 9/2014 | Sobotta | A61N 5/1031 600/1 |
| 2014/0376790 A1 | 12/2014 | Mostafavi | |
| 2015/0208999 A1 | 7/2015 | Steinfeld et al. | |
| 2015/0324967 A1 | 11/2015 | Newell et al. | |
| 2016/0070436 A1 | 3/2016 | Thomas et al. | |
| 2016/0136461 A1* | 5/2016 | Iwata | A61N 5/1079 600/1 |
| 2016/0140300 A1* | 5/2016 | Purdie | A61N 5/103 705/2 |
| 2016/0184605 A1 | 6/2016 | Roberts et al. | |
| 2016/0256714 A1* | 9/2016 | Field | A61N 5/1039 |
| 2017/0203123 A1* | 7/2017 | Requardt | A61N 5/1037 |
| 2017/0209716 A1* | 7/2017 | Lugosi | G16H 20/40 |
| 2018/0043183 A1* | 2/2018 | Sheng | A61N 5/103 |
| 2018/0078786 A1* | 3/2018 | Vik | G16H 20/40 |

FOREIGN PATENT DOCUMENTS

| | | |
|---|---|---|
| DE | 10 2012 203 767 A1 | 7/2013 |
| JP | 2014-128352 | 7/2014 |
| WO | WO 2011/153639 A2 | 12/2011 |
| WO | WO 2015/017630 A1 | 2/2015 |
| WO | WO 2015/017639 A1 | 2/2015 |
| WO | WO 2016/014422 A1 | 1/2016 |

* cited by examiner

SYSTEMS AND METHODS FOR PLANNING AND EXECUTING AUTOMATED MULTI-AXIS MOTION IN TREATMENT

FIELD

This application relates generally to medical treatment, and more specifically, to systems and methods for determining and executing a radiation treatment plan that involves multi-axis motion.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. This allows an accurate and precise dosage of radiation to be delivered to a patient. Embodiments of methods and systems for determining treatment plans that include imaging consideration are described herein.

Also, methods and systems for operating a treatment system that consider patient loading and unloading are described herein.

SUMMARY

An apparatus for creating a radiation treatment plan for execution by a radiation treatment machine, includes: a waypoint module configured to obtain imaging waypoint data representing imaging waypoints, the imaging waypoints at least partially defining one or more positions for obtaining images of a patient during a treatment session; a treatment trajectory module configured to obtain treatment data at least partially defining a beam-on direction; a treatment plan generator configured to create the radiation treatment plan based at least in part on the imaging waypoint data and the treatment data.

Optionally, the imaging waypoint data defines a gantry position, a couch position, a couch orientation, an image energy source position, or any combination of the foregoing, for obtaining one or more of the images of the patient.

Optionally, the treatment data defines a gantry angle or a range of gantry angles for an energy source to deliver treatment energies.

Optionally, the waypoint module is configured to obtain the imaging waypoint data before the treatment trajectory module obtains the treatment data.

Optionally, the treatment trajectory module is configured to obtain the treatment data based on the imaging waypoint data.

Optionally, the imaging waypoint data comprises a user input indicating a desired position for imaging, wherein the treatment trajectory module is configured to obtain the treatment data based on the user input.

Optionally, the treatment trajectory module is configured to obtain the treatment data before the waypoint module obtains the imaging waypoint data.

Optionally, the apparatus further includes a direction proposal generator configured to generate proposed directions where imaging is possible based on the treatment data, wherein the waypoint module is configured to obtain the imaging waypoint data based on one or more of the proposed directions.

Optionally, the apparatus further includes a user interface configured to receive a user input indicating a selected one of the directions, wherein the waypoint module is configured to obtain the imaging waypoint data based on the user input.

Optionally, the treatment data defines a couch position, a couch orientation, a treatment energy source position, or any combination of the foregoing, for delivering one or more treatment energies to the patient.

Optionally, the treatment trajectory module is also configured to determine a set of possible trajectories.

Optionally, the treatment trajectory module is configured to determine the set of possible trajectories based on collision avoidance, imaging capability, or both.

Optionally, the apparatus further includes a user interface for receiving a user input representing a selected one or more of the possible trajectories.

A method for creating a radiation treatment plan for execution by a radiation treatment machine, includes: obtaining imaging waypoint data representing imaging waypoints, wherein the imaging waypoints at least partially define one or more positions for obtaining images of a patient; obtaining treatment data at least partially defining a beam-on direction; creating the radiation treatment plan based at least in part on the imaging waypoint data and the treatment data.

Optionally, the imaging waypoint data defines a gantry position, a couch position, a couch orientation, an image energy source position, or any combination of the foregoing, for obtaining one or more of the images of the patient.

Optionally, the treatment data defines a gantry angle or a range of gantry angles for an energy source to deliver treatment energies.

Optionally, the imaging waypoint data is obtained before the treatment data is obtained.

Optionally, the treatment data is obtained based on the imaging waypoint data.

Optionally, the imaging waypoint data comprises a user input indicating a desired position for imaging, wherein the treatment data is obtained based on the user input.

Optionally, the treatment data is obtained before the imaging waypoint data is obtained.

Optionally, the method further includes generating proposed directions where imaging is possible based on the treatment data, wherein the imaging waypoint data is obtained based on the proposed directions.

Optionally, the method further includes receiving a user input indicating a selected one of the directions, wherein the imaging waypoint data is obtained based on the user input.

Optionally, the treatment data defines a couch position, a couch orientation, a treatment energy source position, or any combination of the foregoing, for delivering one or more treatment energies to the patient.

Optionally, the method further includes determining a set of possible trajectories.

Optionally, the set of possible trajectories is determined based on collision avoidance, imaging capability, or both.

Optionally, the method further includes receiving a user input representing a selected one or more of the possible trajectories.

A apparatus for controlling a medical system comprising a treatment machine and a patient supporting device, includes: one or more input(s) for obtaining a current position associated with the patient supporting device, and a desired position associated with the patient supporting device to be achieved; a trajectory module configured to determine trajectories for one or more components of the treatment system, and an order of the trajectories, based on the current position and the desired position associated with the patient supporting device; and a control signal generator for outputting one or more control signal(s) to operate the one or more components of the treatment system based on the determined trajectories and the order of the trajectories.

Optionally, the trajectory module determines the trajectories and the order of the trajectories using a shortest-path algorithm.

Optionally, the current position occurs when a treatment is stopped, and the desired position is for unloading a patient.

Optionally, the current position is for loading a patient, and the desired position is for delivering treatment to the patient.

Optionally, the control signal generator is configured to output the one or more control signal(s) to move one or more components of the treatment machine to open up a path for one or more components of the patient supporting device, and to move one of the one or more components of the patient supporting device after the one or more components of the treatment machine is moved.

A method of operating a medical system comprising a treatment machine and a patient supporting device, includes: obtaining a current position associated with the patient supporting device; obtaining a desired position associated with the patient supporting device to be achieved; determining, by a trajectory module, trajectories for one or more components of the treatment system, and an order of the trajectories, based on the current position and the desired position associated with the patient supporting device; and operating the one or more components of the treatment system based on the determined trajectories and the order of the trajectories.

Optionally, the trajectory module determines the trajectories and the order of the trajectories using a shortest-path algorithm.

Optionally, the current position occurs when a treatment is stopped, and the desired position is for unloading a patient.

Optionally, the current position is for loading a patient, and the desired position is for delivering treatment to the patient.

Optionally, the act of operating the one or more components of the treatment system comprises moving one or more components of the treatment machine to open up a path for one or more components of the patient supporting device, and moving one of the one or more components of the patient supporting device after the one or more components of the treatment machine is moved.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
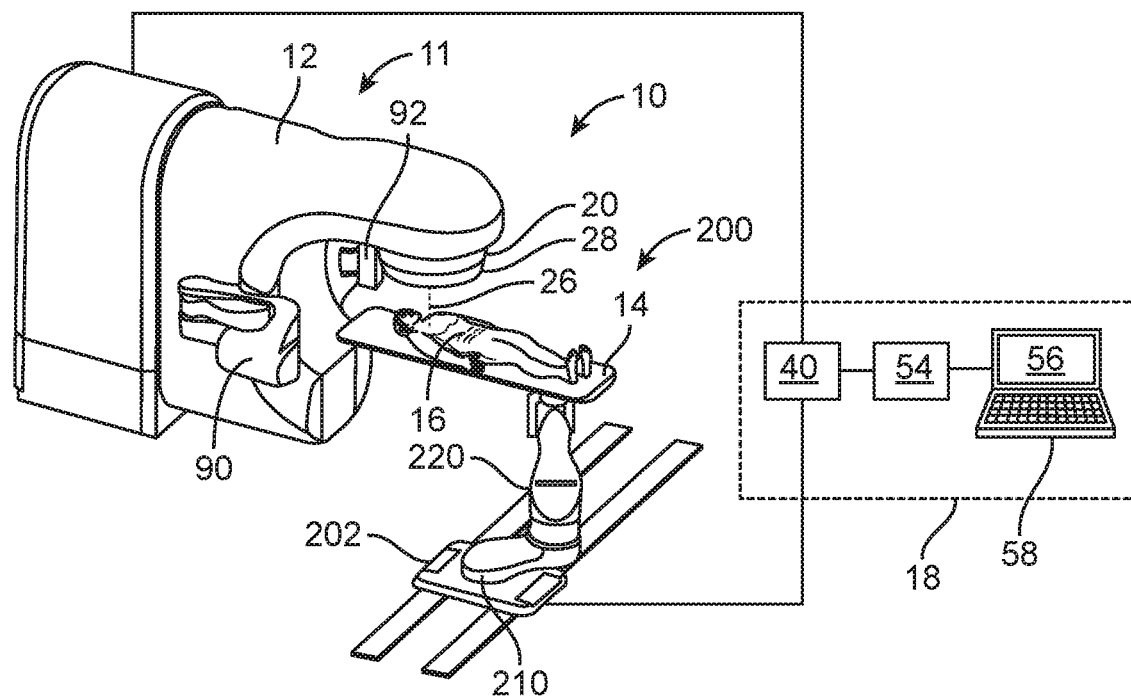
FIG. 1 illustrates a medical system for delivering treatment radiation with a patient supporting device in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a medical system 10 including a treatment machine 11 for delivering radiation. The treatment machine 11 includes a gantry 12 in a form of an arm. The treatment machine 11 also includes an energy output 20 that outputs a beam 26 of radiation towards a patient 16 while the patient 16 is supported on platform 14, and a collimator system 28 for controlling a delivery of the radiation beam 26. The energy output 20 can be configured to output a cone beam, a fan beam, or other types of radiation beams in different embodiments.

In the illustrated embodiments, the treatment machine 11 includes a treatment radiation source for providing treatment radiation energy. In other embodiments, in addition to being a treatment radiation source, the radiation source 20 can also be a diagnostic radiation source for providing diagnostic energy. In such cases, the treatment machine 11 will include an imager located at an operative position relative to the energy output 20 (e.g., under the platform 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source is able to generate X-ray radiation at a plurality of photon energy levels within a range anywhere between approximately 10 keV and approximately 20 MeV. Radiation sources capable of generating X-ray radiation at different energy levels are described in U.S. Pat. No. 6,888,919, entitled "RADIOTHERAPY APPARATUS EQUIPPED WITH AN ARTICULABLE GANTRY FOR POSITIONING AN IMAGING UNIT," filed on Nov. 2, 2001, and U.S. Pat. No. 7,649,981, entitled "MULTI-ENERGY X-RAY SOURCE," filed on Oct. 15, 2003. In further embodiments, the radiation source can be a diagnostic radiation source. In the illustrated embodiments, the energy output 20 is rotatably coupled to the gantry 12. In other embodiments, the energy output 20 may be located within a bore (instead of being located at an arm).

The medical system 10 also includes a control system 18 for controlling an operation of the treatment machine 11. In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). The operation of the radiation source, the collimator system 28, and the gantry 12 (if the gantry 12 is rotatable), are controlled by the control 40, which provides power and timing signals to the radiation source and the collimator system 28, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

As shown in the figure, the platform 14 is a part of a patient supporting device 200. The patient supporting device includes a base 202, a first member 210, a second member 220, and the platform 14. The patient supporting device 200 will be described in further detail below.

In some embodiments, the treatment machine 11 may optionally include one or more imaging devices. For example, as shown in FIG. 1, the treatment machine 11 may further include a x-ray source 90 and an imager 92 located opposite from the x-ray source 90. The x-ray source 90 and the imager 92 may be configured to image the patient 16 before a delivery of treatment energy (e.g., for patient setup), and/or during a treatment energy delivery session (e.g., between deliveries of radiation beams). In other embodiments, the treatment machine 11 may not include the x-ray source 90 and the imager 92.

It should be noted that the treatment machine 11 is not limited to the configuration described above, and that the treatment machine 11 may have other configurations in other embodiments. For example, in other embodiments, the treatment machine 11 may have a different shape. In other embodiments, the energy output 20 of the treatment machine 11 may have different ranges of motions and/or degrees of freedom. For example, in other embodiments, the energy output 20 may be rotatable about the patient 16 completely through a 360° range, or partially through a range that is less than 360°. Also, in other embodiments, the energy output 20 is translatable relative to the patient 16. In further embodiments, the gantry 12 may be a ring gantry with a bore, and the energy output 20 may be located inside the bore of the gantry 12.

Figure 2:
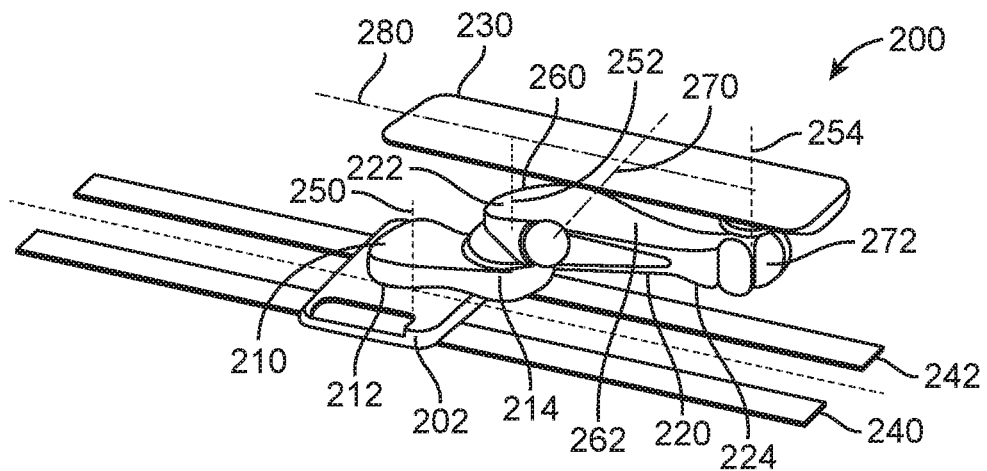
FIG. 2 illustrates the patient supporting device of FIG. 1.

FIG. 2 illustrates the patient supporting device 200 of FIG. 1. As shown in the figure, the patient supporting device 200 has a base 202, a first member 210 with a first end 212 and a second end 214, a second member 220 with a first end 222 and a second end 224, and a platform 230 (the platform 14 of FIG. 1). The base 202 is optionally configured to move along a pre-determined path along a first rail 240 and a second rail 242. The first end 212 of the first member 210 is rotatably coupled to the base 202 so that the first member is rotatable relative to the base 202 about a first vertical axis 250. The first end 222 of the second member 220 is rotatably coupled to the second end 214 of the first member 210 so that the second member is rotatable relative to the first member 210 about a second vertical axis 252. The platform 230 is rotatably coupled to the second end 224 of the second member 220 so that the platform is rotatable relative to the second member 220 about a third axis 254.

In the illustrated embodiments, the second member 220 has a first member portion 260 and a second member portion 262. The first member portion 260 is rotatably coupled to the second member portion 262 so that the first member portion 260 can rotate relative to the second member portion 262 about a first horizontal axis 270. The platform 230 is rotatably coupled to the second member portion 262 so that the platform 230 can rotate relative to the second member portion 262 about a second horizontal axis 272. During use, the platform 230 can rotate relative to the second member portion 262 about the second horizontal axis 272, and the second member portion 262 can rotate relative to the first member portion 260 about the first horizontal axis 270, in synchronization, so that the platform 230 can move vertically (e.g., up and/or down).

Also, in the illustrated example, the platform 230 may be configured to rotate about its longitudinal axis 280.

In the example shown in the figure, the first member 210 is in a form of an arm, and the second member 220 is also in a form of an arm. Also, the first member portion 260 may be considered to be a part of an arm, and the second member portion 260 may be considered to be another part of the arm. In other embodiments, the first member 210 may have other form and/or shape, and may not necessarily be an arm. Similarly, in other embodiments, the second member 220 may have other form and/or shape, and may not necessarily be an arm.

In the illustrated embodiments, the base 202 is configured to move along a pre-determined path defined by the first rail 240 and/or the second rail 242. The first rail 240 and the second rail 242 have a rectilinear configuration, and therefore the base 202 is configured to move in a rectilinear path.

In other embodiments, the rails 240, 242 may have a curvilinear configuration (e.g., an arc, a circular shape, etc.).

Figure 3:
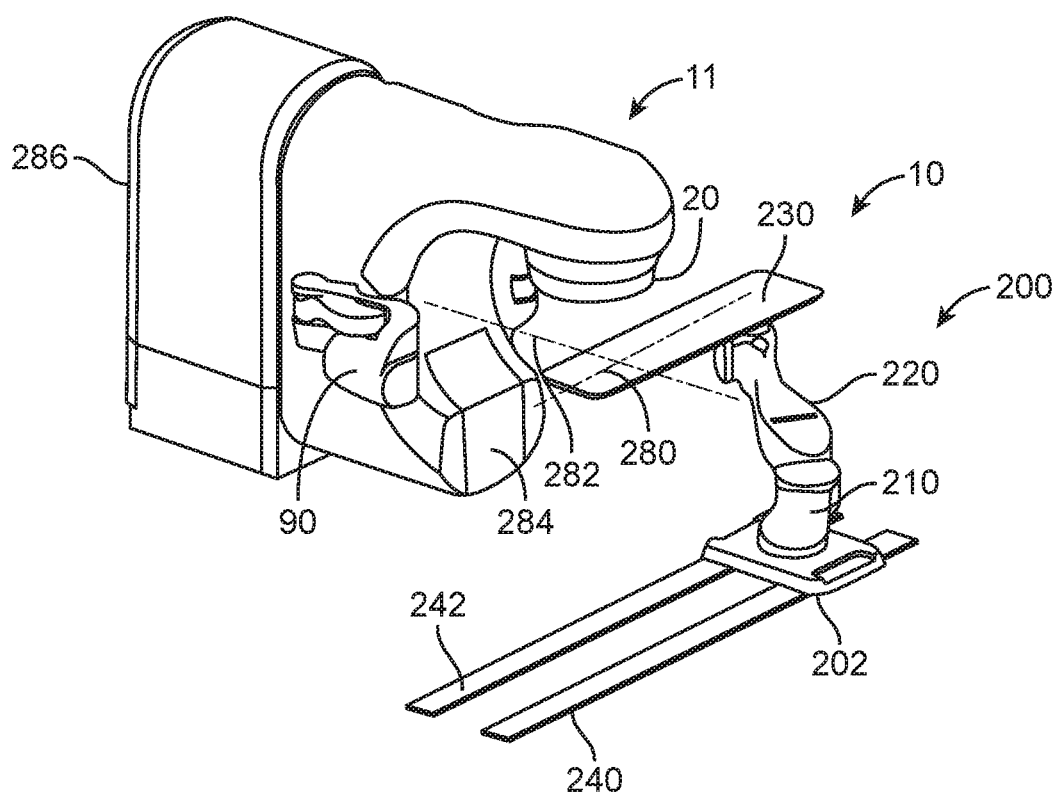
FIG. 3 illustrates the medical system of FIG. 1, particular showing the patient supporting device having a different configuration.

The configuration of the patient supporting device 200 is advantageous because it allows the platform 230 to be placed at different positions with respect to the treatment machine 11. For example, as shown in FIG. 3, the patient supporting device 200 may be operated to place the platform 230 at an orientation, where a longitudinal axis 280 of the platform 230 is perpendicular to a machine axis 282 extending from a front 284 of the treatment machine 11 to a back 286 of the treatment machine 11. Also, having the platform 230 on rails is advantageous because it allows the platform 230 to be moved from one position to another position quickly.

Figure 4:
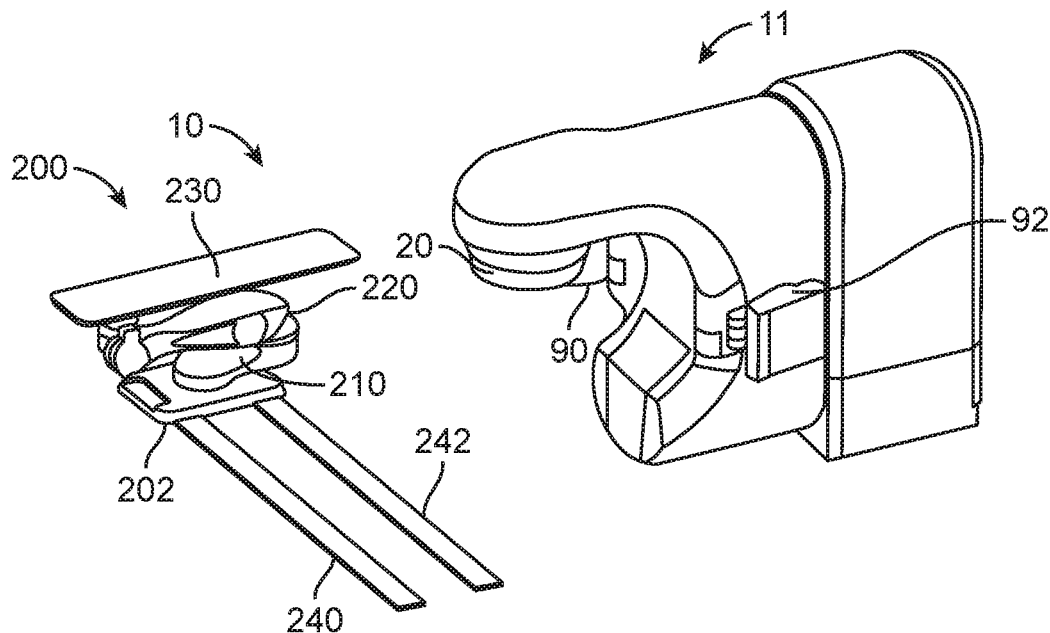
FIG. 4 illustrates the medical system of FIG. 1, particular showing the patient supporting device having a different configuration.

Also, before treatment is initiated, or after treatment is completed, the patient supporting device 200 may have the configuration shown in FIG. 4. In particular, the platform 230, the first member 210, the second member 220, and the base 202 collectively form a S-configuration that minimizes the extent of the space occupied by the patient supporting device 200. In such configuration, the patient supporting device 200 does not occupy significant space, and the patient supporting device 200 may allow the patient to conveniently get onto the platform 230 and/or to leave the platform 230.

Figure 5A:
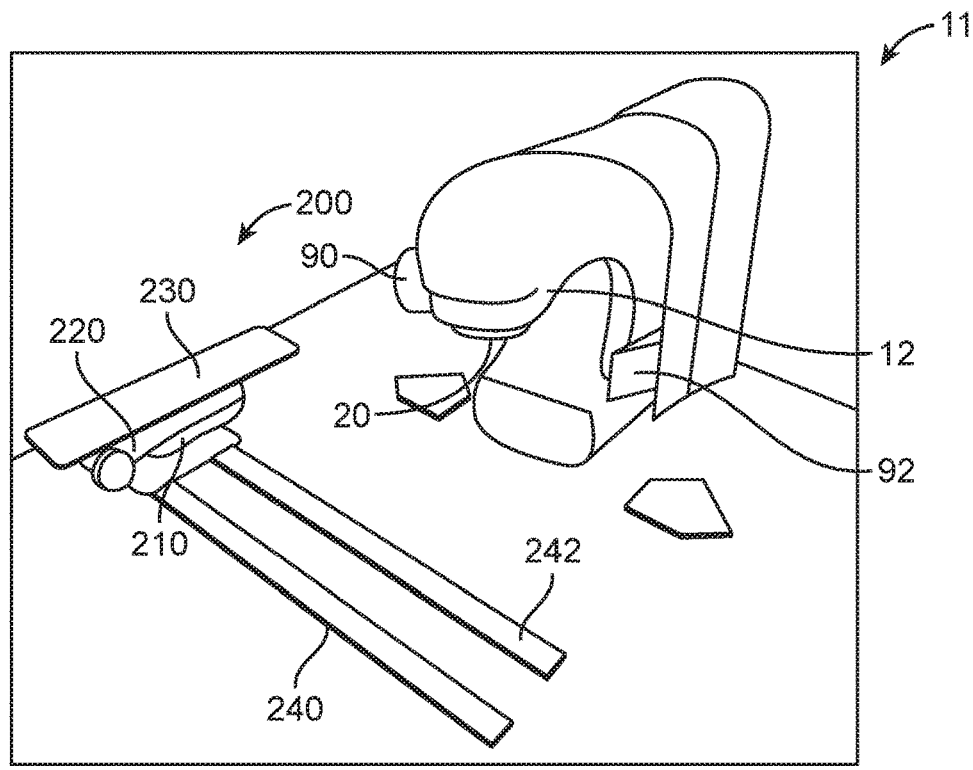
FIGS. 5A-5L illustrate the medical system of FIG. 1, particular showing different movement configurations for the treatment machine and the patient supporting device.

FIGS. 5A-5L illustrate examples of configurations that may be achieved by the patient supporting device 200 during a medical method. As shown in FIG. 5A, the patient supporting device 200 may be in a park position. While in the park position, the platform 230 is located above the second member 220, and the second member 220 is located above the first member 210. This configuration allows the patient supporting device 200 to be parked while minimizing the amount of space occupied by the patient supporting device 200. In some embodiments, the patient may be placed at the platform 230 while the patient supporting device 200 is in such park position. In other embodiments, the platform 230 may be moved to a patient-loading position for loading the patient onto the platform 230. For example, the base 202 of the patient supporting device 200 may be translated to move the platform 230 away from the park position to a patient-loading position. The patient may then be placed onto the platform 230.

Figure 5B:
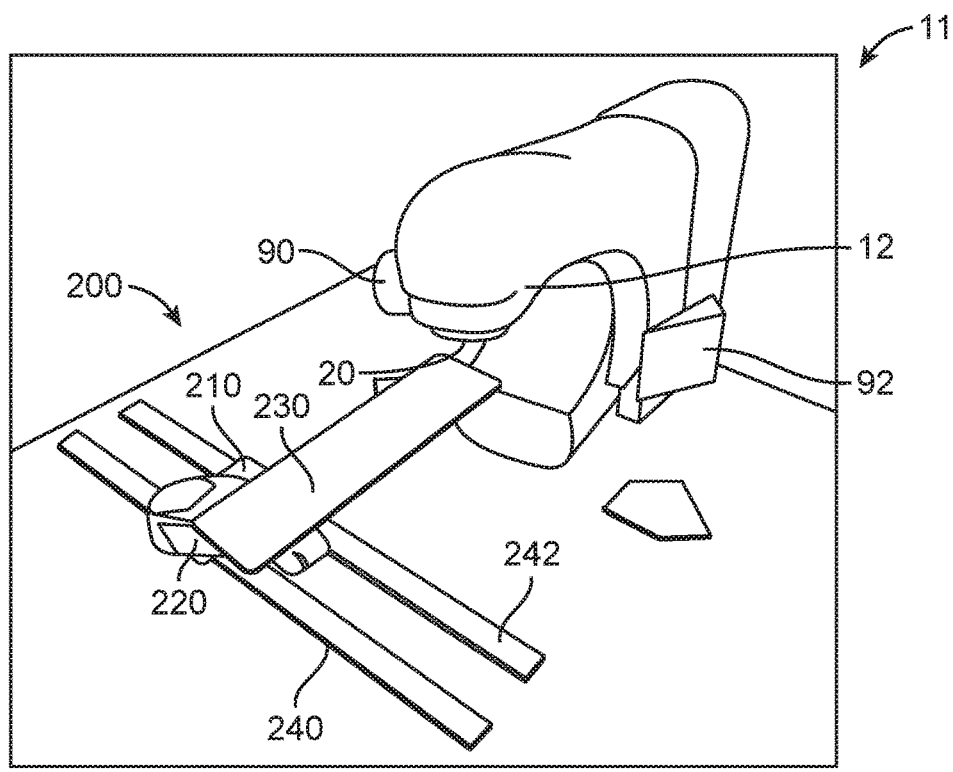

Next, the patient supporting device 200 may be operated to move the platform 230 so that the longitudinal axis 280 of the platform 280 corresponds with the machine axis 282 (FIG. 5B). For example, the base 202 may be translated along the rails, the first member 210 may be rotated relative to the base 202, the second member 220 may be rotated relative to the first member 210, the platform 230 may be rotated relative to the second member 220, or any combination of the foregoing may be performed, in order to desirably position the platform 230. While in the configuration shown, a patient setup procedure may be performed to align the patient with respect to the treatment machine 11. For example, certain region of the patient may be placed at the treatment position (e.g., isocenter position) with respect to the treatment machine 11.

After the patient setup procedure, the treatment machine 11 may then be operated to treat the patient. For example, as shown in FIG. 5C, the arm of the treatment machine 11 may be rotated to thereby place the energy output 20 at different gantry angles to deliver energies towards the patient from different angles.

Figure 5C:
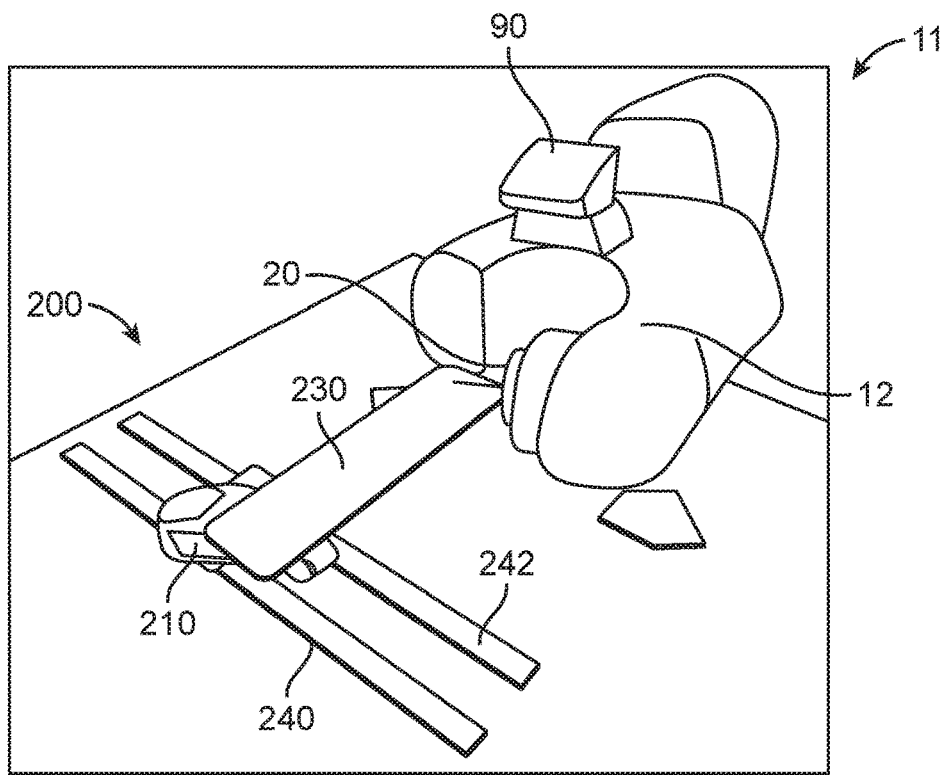

In the example shown in FIG. 5C, the energy output 20 rotates around the treatment position while the platform 230 is at an orientation where the longitudinal axis 280 of the platform 230 corresponds with the machine axis 282 of the treatment machine 11. In other embodiments, the platform 230 may be positioned such that the longitudinal axis 280 of the platform 230 is at an acute angle, at a 90° angle, or at an angle that is larger than 90° but less than 180°, with respect to the machine axis 282. While the platform 230 is at such position, the energy output 20 of the treatment machine 11 may be rotated around the treatment position to deliver energies towards the patient from different gantry angles.

Figure 5D:
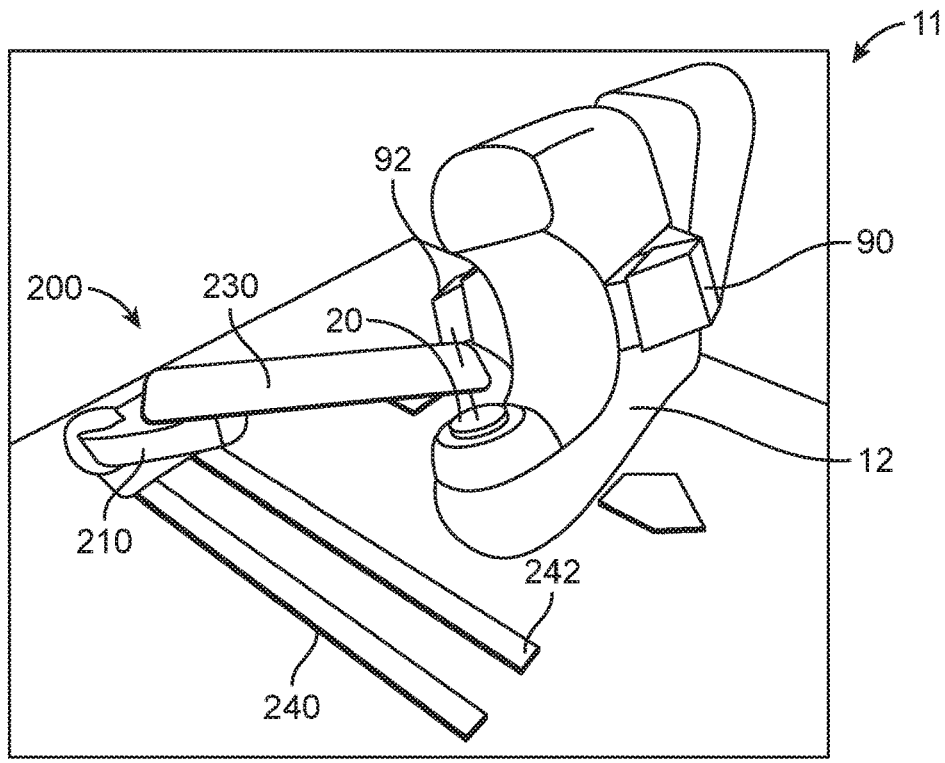
Figure 5E:
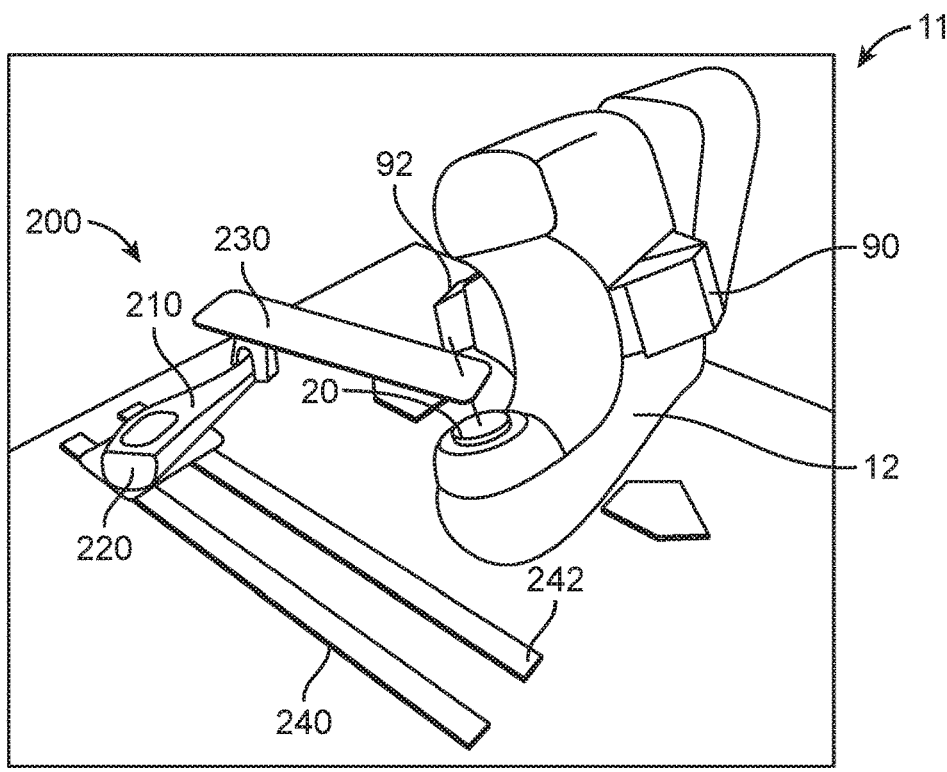
Figure 5F:
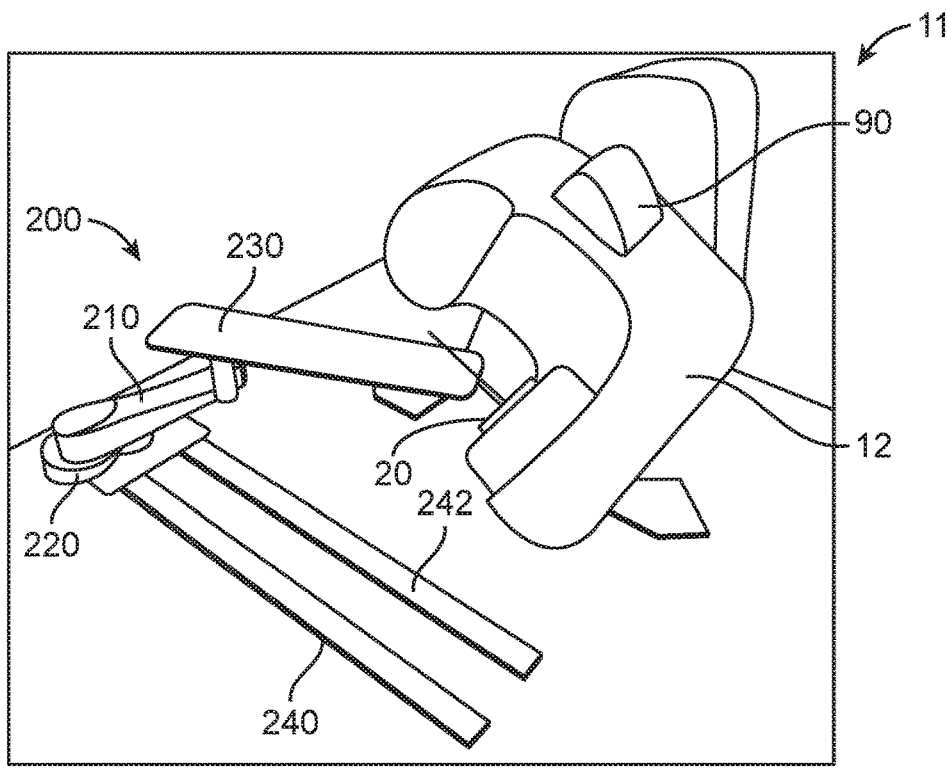
Figure 5G:
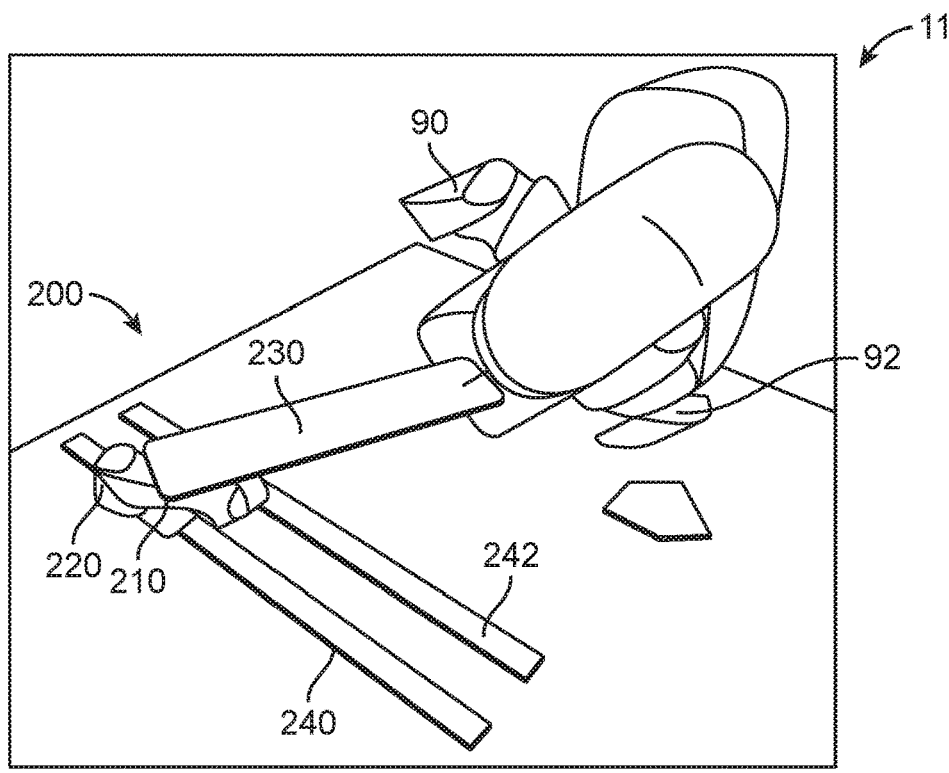
Figure 5H:
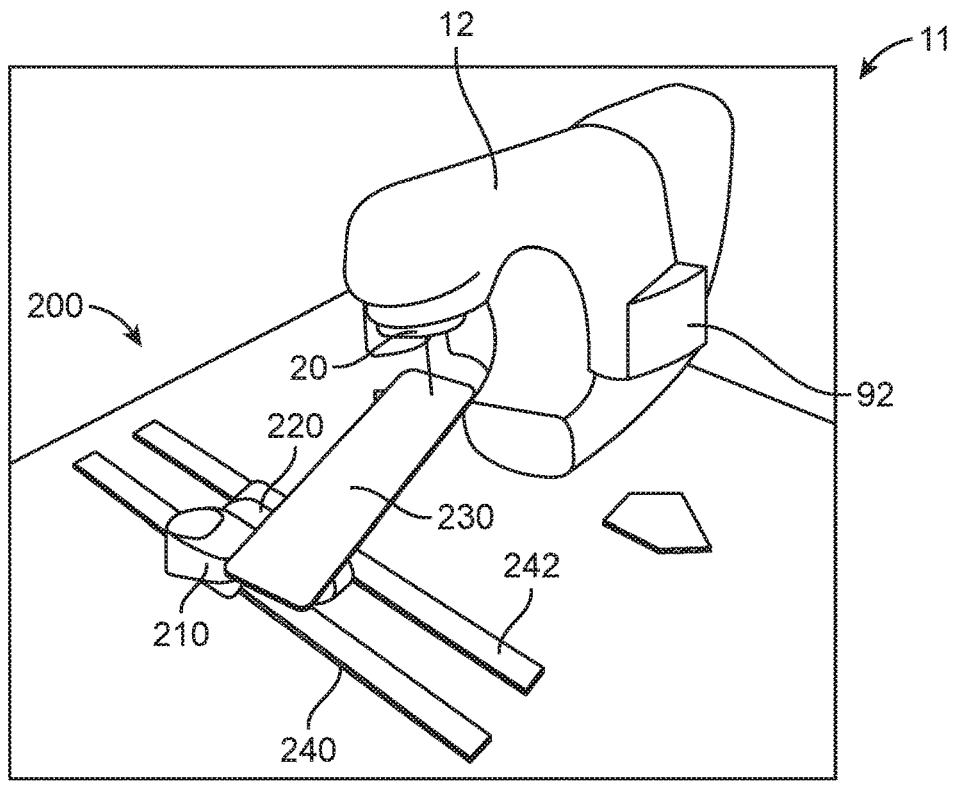
Figure 5I:
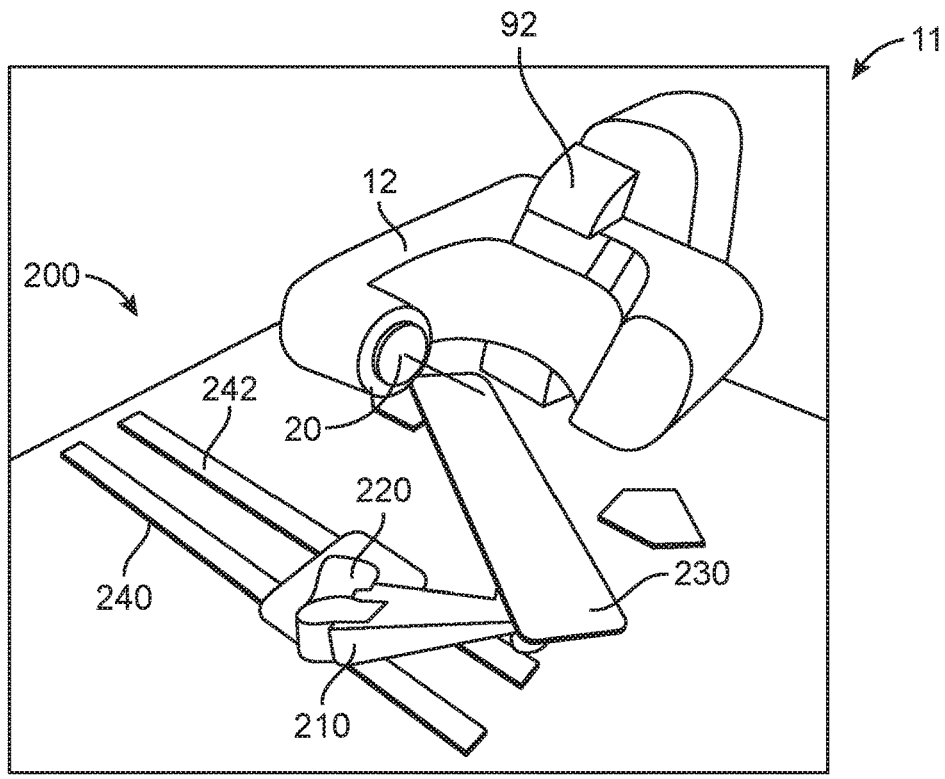
Figure 5J:
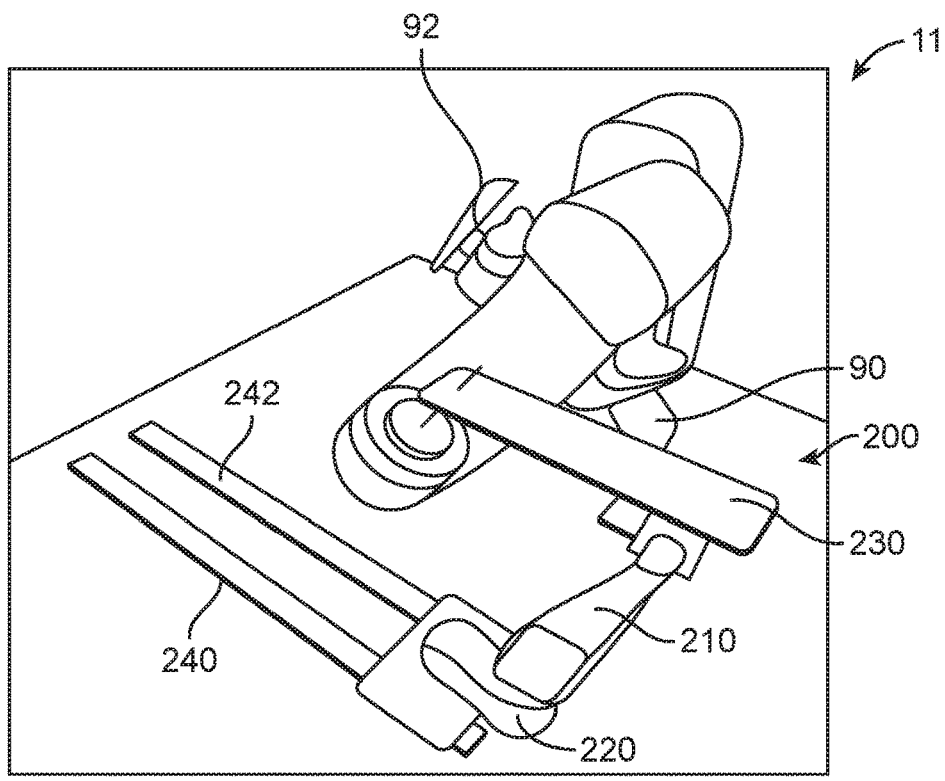
Figure 5K:
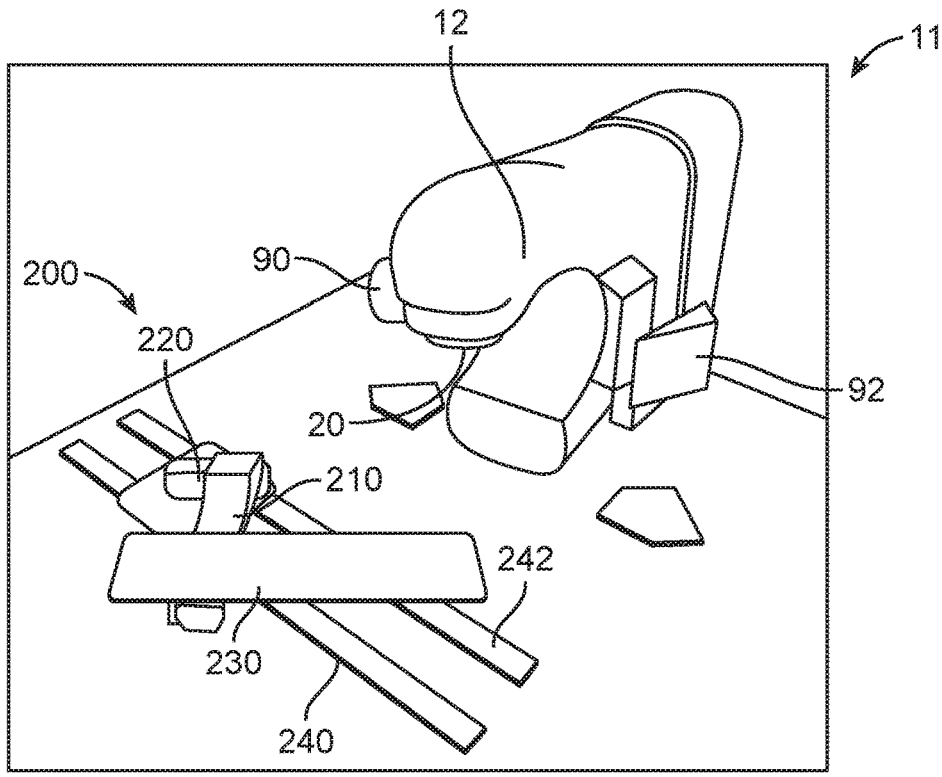
Figure 5L:
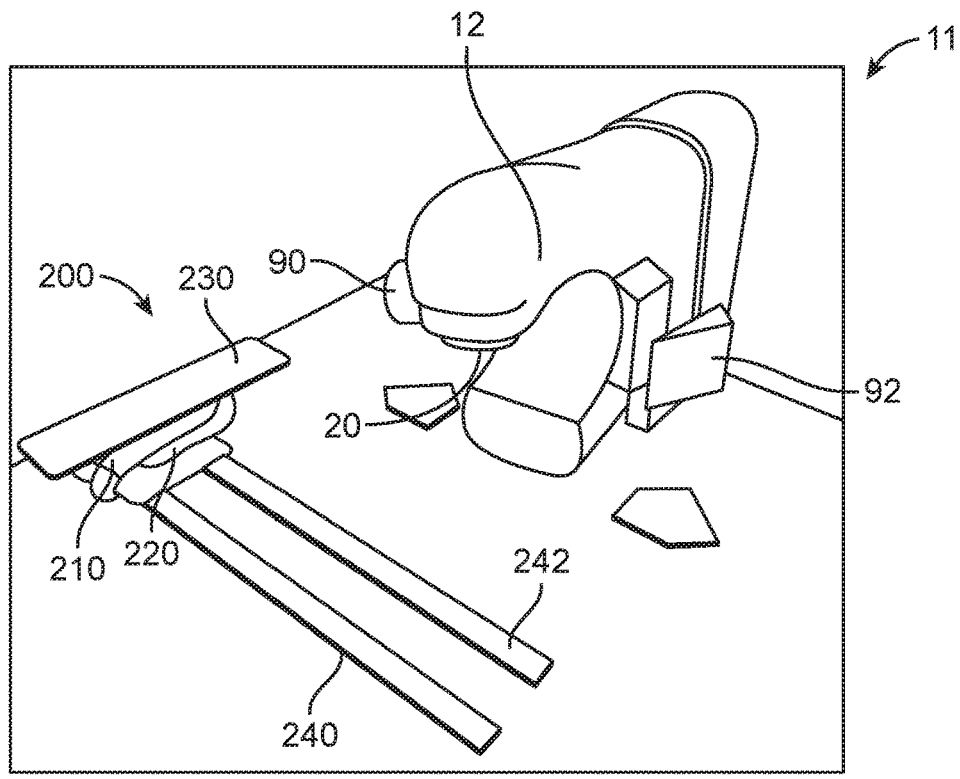

In some cases, instead of rotating the energy output 20 around the treatment position while the platform 230 is stationary, the platform 230 may be positioned while the energy output 20 is stationary. For example, as shown in FIGS. 5D-5E, while the arm with the energy output 20 is stationary at the position shown, the patient supporting device 200 may be operated to rotate the platform 230 from the position shown in FIG. 5C to the position shown in FIG. 5D, and also from the position shown in FIG. 5D to the position shown in FIG. 5E. Such movement results in a portion of the platform 230 remaining in a field-of-view of the energy output 20 while the platform 230 is rotated within a horizontal plane. In some cases, a surface point of the platform 230 may remain stationary while the platform 230 is rotated about a vertical axis extending through the surface point.

In one implementation, the above movement of the platform 230 (from the position of FIG. 5C to the position of FIG. 5D, and then to the position of FIG. 5E) may be achieved by moving the platform 230 relative to the second member 220, moving the second member 220 relative to the first member 210, moving the first member 210 relative to the base 202, moving the base 202, or any combination of the foregoing. In some cases, if multiple components of the patient supporting device 200 are moved, the multiple components may be moved simultaneously. Alternatively, the multiple components may be moved in sequence such that one component is moved first, and then another component is moved afterwards. In either case, the energy output 20 may deliver treatment energy towards the patient while one or more of the components (e.g., the base 202, the first member 210, the second member, 220, the platform 230, etc.) of the patient supporting device 200 are moving, or when the components of the patient supporting device 200 have stopped moving. For example, when the platform 230 is moved along a path, the components of the patient supporting device 200 may stop moving at certain points along the path to allow the energy output 20 of the treatment machine 11 to deliver energies towards the patient.

In the above example, the energy output 20 is located below the elevation of the platform 230 while the platform 230 is rotated about a vertical axis extending through a field-of-view of the energy output 20. In other embodiments, the energy output 20 may be at other positions while the platform 230 is rotated about the vertical axis. For example, the energy output 20 of the treatment machine 11 may be directly above the platform 230, at the same elevation as that of the platform 230, or may be at other positions that are above or below the elevation of the platform 230.

In some cases, instead of moving (e.g., rotating) the platform 230 while the energy output 20 of the treatment machine 11 is stationary, both the platform 230 and the energy output 20 of the treatment machine 11 may be positioned. For example, as shown in FIGS. 5E-5J, the platform 230 and the energy output 20 of the treatment machine 11 may be moved simultaneously so that the platform 230 and the energy output 20 are moved from the respective positions shown in FIG. 5E to the respective positions in FIG. 5F, and then to the respective positions in FIG. 5G, and then to the respective positions in FIG. 5H, and then to the respective positions in FIG. 5I, and then to the respective positions in FIG. 5J.

In one implementation, the above movement of the platform 230 (from the position of FIG. 5E to the position of FIG. 5F, to the position of FIG. 5G, to the position of FIG. 5H, to the position of FIG. 5I, and to the position of FIG. 5J) may be achieved by moving the platform 230 relative to the second member 220, moving the second member 220 relative to the first member 210, moving the first member 210 relative to the base 202, moving the base 202, or any combination of the foregoing. In some cases, if multiple components of the patient supporting device 200 are moved, the multiple components may be moved simultaneously. Alternatively, the multiple components may be moved in sequence such that one component is moved first, and then another component is moved afterwards. In either case, the energy output 20 may deliver treatment energy towards the patient while one or more of the components (e.g., the base 202, the first member 210, the second member, 220, the platform 230, etc.) of the patient supporting device 200 are moving, and/or while the energy output 20 is moving. Alternatively, the energy output 20 may deliver treatment energy towards the patient when the components of the patient supporting device 200 have stopped moving, and when the energy output 20 has stopped moving. For example, when the platform 230 is moved along a path, the components of the patient supporting device 200 may stop moving at certain points along the path to allow the energy output 20 of the treatment machine 11 to deliver energies towards the patient. Similarly, when the energy output 20 of the treatment machine 11 is moved along a path, the energy output 20 may stop moving at certain points along the path to allow the energy output 20 to deliver energies towards the patient. Alternatively, the delivery of energies may occur simultaneously while the components of the patient supporting device 200 are moving, and/or while the energy output 20 of the treatment machine 11 is moving.

After the patient has been treated, the platform 230 may then be moved to a patient-unloading position to unload the patient. For example, the patient supporting device 200 may be operated to move the platform 230 to the position shown in FIG. 5K. Alternatively, the patient supporting device 200 may be operated to move the platform 230 to the position shown in FIG. 5L.

As illustrated in the above embodiments, the patient supporting device 200 is advantageous because the patient supporting platform 230 (and therefore the patient) to be placed at a variety of positions and orientations with respect to the treatment machine 11. In combination with the movement of the energy output 20 of the treatment machine 11, the various degrees of movement of the patient supporting device 200 allow treatment energies to be delivered to the patient from many different angles that were not possible in existing solutions. Also, the configuration of the patient supporting device 200 allows larger reach to other machines next to the treatment machine, and increases positional flexibility. Furthermore, because the patient supporting device 200 can be folded to assume a narrow profile, the patient supporting device 200 can be parked close to a wall. In addition, the length of the rail system (including the rails 240, 242) can be easily adapted according to treatment room size or usage of the system. This flexibility allows installations of the rail system and the patient supporting device 200 for various different room layouts.

Also, the movement of the base 202 along a path (e.g., along one or more rails) is advantageous because it may allow the platform 230 to be moved to a certain position faster and more effectively. If the base 202 is not moveable along a path, it may take longer for the platform 230 to reach certain positions because of the articulation of the arm relative to the room and the treatment machine.

It should be noted that the movements and positioning of the various components of the patient supporting device 200 should not be limited to the examples described, and that the patient supporting device 200 may achieve other types of movements and positioning. For example, in other embodiments, the platform 230 may be translated vertically (e.g., up and/or down) while the orientation of the platform 230 is maintained. Such may be accomplished by synchronously rotating the second member 220 relative to the first member 210 about the first horizontal axis in a first direction, and simultaneously rotating the platform 230 relative to the second member 220 about the second horizontal axis in a second direction that is opposite the first direction. In other embodiments, the platform 230 may be translated horizontally along a path that corresponds with (e.g., parallel to) the machine axis 282 of the treatment machine 11. Such may be accomplished by synchronously rotating the first member 210 relative to the base 202 about the first axis 250 in a first direction, rotating the second member 220 relative to the first member 210 about the second axis 252 in a second direction opposite the first direction, and rotating the platform 230 relative to the second member 220 about the third axis 254 in the first direction. In still further embodiments, the platform 230 may be translated horizontally along a path that is parallel to the floor. Such may be accomplished by translating the base 202.

Also, in any of the embodiments described herein, the patient supporting device 200 may be configured to move at a speed that is sufficient for dynamic treatment. For example, the patient supporting device 200 may be configured to move in a path with a speed that corresponds (e.g., complements) with a motion speed of the treatment machine 11 (e.g., the speed of the rotating energy output 20) and/or the rate at which treatment energies are being delivered. Also, in some cases, the patient supporting device 200 may be configured to move with a sufficiently fast speed to allow the patient supporting device 200 to compensate for a breathing motion of the patient. For example, the patient supporting device 200 may be configured to move the patient in order to at least partially compensate for a breathing motion of the patient, thereby allowing breathing gating to be used to deliver treatment energies.

In addition, in any of the embodiments described herein, the patient supporting device 200 may be configured to move the platform 230 in synchronization or in correspondence with a movement or position of the energy output 20. For example, the platform 230 may be moved so that a point at the patient (e.g., an isocenter) is maintained at a certain prescribed distance or a certain prescribed range of distances from the energy output 20. Accordingly, regardless of the position of the energy output 20, the isocenter is maintained at a fixed distance or within a fixed distance range from the energy output 20. The movement of the platform 230 may be dynamically performed simultaneously with a movement of the energy output 20. Alternatively, the movement of the platform 230 may be performed after the energy output 20 has moved, so that the movements of the platform 230 and the energy output 20 are staggered. Furthermore, in some cases, the source-axis-distance (SAD) may be extended compared to the scenario in which the platform 230 is stationary and the energy output 20 is rotated around the platform 230. Such can be accomplished by moving the platform 230 in a direction that is away from the energy output 20, thereby increasing the SAD. During treatment, as the energy output 20 rotates around a space, the patient supporting device 200 also rotates the platform 230 around the same space in synchronization or in correspondence with the energy output 20. This allows the energy output 20 to always be aimed at a treatment target in the patient supported on the platform 230, which both the energy output 20 and the platform 230 on opposite sides of the space are rotated in correspondence with each other.

In the above embodiments, the treatment machine 11 has been described as having a rotatable arm that includes an energy output 20 and a collimator. In other embodiments, instead of the rotatable arm, the treatment machine 11 may have a ring gantry that carries the energy output 20. In such cases, during treatment, the patient supporting device 200 may be operated to place a part of the patient into a bore, and the ring gantry may be rotated around the patient to allow the energy output 20 to deliver treatment energies from different angles.

In addition, in any of the embodiments described herein, the platform 230 may be a removeable couch top. For example, the platform 230 may be detachably coupled to a connector that is at the second end of the second member 220. In some cases, the platform 230 may be removed from the rest of the patient supporting device 200, and the patient may be placed on top of the platform 230 for patient setup. The placement of the patient on the platform 230 may be performed in the treatment room where the patient supporting device 200 is located, or may be performed in another room. In one implementation, the patient may be positioned such that a reference location at the patient relative to the platform 230 is achieved. After that is set up, the platform 230 with the patient may then be attached to the connector at the patient supporting device 200. Furthermore, in some embodiments, the movement of the platform 230 with the patient to attach the platform 230 with the rest of the patient supporting device 200 may be performed automatically using a robotic device (e.g., a tool-changer).

In further embodiments, the patient supporting device 200 may also include one or more positional indicators for allowing a position of the patient supporting device 200 to be determined. For example, the patient supporting device 200 may include a positioning system that allows its position relative to some global coordinate system be determined. The positioning system may include one or more components at the platform 230, one or more components at the first member 210, one or more components at the second member 202, one or more components at the base 202, or any combination of the foregoing. The component may be a signal emitter, a signal receiver, a fiducial, a marker, etc. In other embodiments, a component may be a sensor for sensing a signal, or may be a fiducial that is configured for sensing, that can be used to derive a position.

In another example, the patient supporting device 200 may include multiple positional indicators at the respective moving parts (e.g., the base 202, the first member 210, the first member portion 260 of the second member 220, the second member portion 262 of the second member 220, and the platform 230). The positional indicators may have respective energy sources for emitting positional energies (beacons), and there may be one or more detectors in the treatment room for detecting such positional energies. Based on the detected positional energies, the processing unit may then determine the positions and orientations of the various components of the patient supporting device 200. In other embodiments, the beacons may be passive devices.

In another example, the positional indicators may include one or more markers at the platform 230, one or more markers at the first member 210, one or more markers at the second member 220, and one or more markers at the base 202. The markers may be configured to be detected using one or more cameras, or other types of sensing device(s).

In further embodiments, the patient supporting device 200 may include an imaging system for imaging the patient. For example, the patient supporting device 200 may include an energy source for providing imaging energy, and an imager for generating an image of a patient (e.g., an internal part of the patient) based on the imaging energy after it has penetrated through the patient. By means of non-limiting examples, the imaging system at the patient supporting device 200 may be a radiation imaging system, an ultrasound imaging system, a MRI system, a fluoroscope, a CT system, a PET system, a SPECT system, a CT-PET system, etc. During use, the imaging system at the patient supporting device 200 may be used to image the patient to determine a position and/or a shape of target and/or critical organ. Such may be performed during a patient setup procedure, and/or during treatment (e.g., between deliveries of treatment energies).

Also, in any of the embodiments described herein, instead of having the platform 230 that is completely horizontal to support the entire patient horizontally, the platform 230 may have other configurations in other embodiments. For example, in other embodiments, the platform 230 may have a form of a chair to support the patient in an upright position. In one implementation, the platform 230 may have a first platform portion and a second platform portion that is rotatably coupled to the first platform portion. The platform portions may be operated so that both platform portions are oriented horizontally, thereby providing a completely horizontal supporting surface for supporting the patient horizontally. In another method of use, one of the platform portions may be rotated to be in an upright position, thereby creating a chair-like supporting structure for supporting the patient in an upright position.

Furthermore, in any of the embodiments described herein, the patient supporting device 200 may include one or more force and/or torque sensor for load measurement. In one implementation, the platform 230 may have a force sensor for measuring an amount of load being supported by the platform 230. The measurement may be transmitted to a processing unit, which calculates an amount of deflection resulted from such load. The processing unit may then operate the patient supporting device 200 (e.g., rotate the platform 230 about a horizontal axis that is perpendicular to the longitudinal axis of the platform 230) to compensate for such deflection. Because the patient supporting device 200 is configured to support load using cantilever-action, the amount of deflection due to heavy load supported by the platform 230 may be significant. The above feature may allow the deflection to be compensated. In other embodiments, the patient supporting device 200 may not support load using cantilever-action, and the deflection due to patient load on the platform 230 may not be significant.

In addition, in any of the embodiments described herein, the patient supporting device 200 and/or the treatment machine 11 may include one or more cameras for monitoring the patient. The one or more cameras may be used to sense one or more markers (e.g., one or more light emitting or light reflecting markers, one or more reference locations at the patient that function as marker(s), etc.). In some embodiments, the sensed markers may be used to determine a position of a patient part. For example, the sensed markers may be positionally related to a breathing movement of the patient. In such cases, the sensed markers may be processed by a processing unit, which determines one or more breathing phases of the patient. Also, in some embodiments, the one or more cameras may generate images for monitoring a position of the patient. The processing unit may process such images to ensure that the patient is at an intended position, and/or to provide collision detection and avoidance. It should be noted that one or more of the camera(s) may be a depth sensing camera. In one implementation, the patient supporting device 200 may include a depth sensing camera attached thereto. During use, the depth sensing camera detects a surface of the patient, and the processing unit generates a surface model representing the surface of the patient. While treatment is being performed, the patient supporting device 200 and the treatment machine 11 may move. The processing unit monitors objects next to the patient. If the processing unit determines that an object (e.g., the arm 12 of the treatment machine 11) is getting too close to the patient (e.g., within a threshold distance from the surface model), the processing unit may then generates a warning signal and/or a control signal to stop or pause the treatment. For example, the processing unit may generate a control signal to stop a movement of the treatment machine 11 and/or a movement of the patient supporting device 200. The processing unit may also generate a control signal to stop a delivery of treatment energies by the treatment machine 11. In some cases, one or more proximity sensors may be employed to determine whether the patient is too close to component(s) of the treatment machine 11.

Also, in the above embodiments, the treatment machine 11 has been described with reference to providing treatment radiation. In other embodiments, the treatment machine 11 may be configured to provide other types of treatment energy. For examples, in other embodiments, the treatment machine 11 may be configured to provide proton beam for proton therapy, treatment ultrasound energy, radiofrequency energy, etc. In addition, in other embodiments, the radiation source may be a proton source for delivering protons to treat a patient, an electron source for delivering electrons, or other types of particle source for delivering other types of particles for treating patient.

Figure 6A:
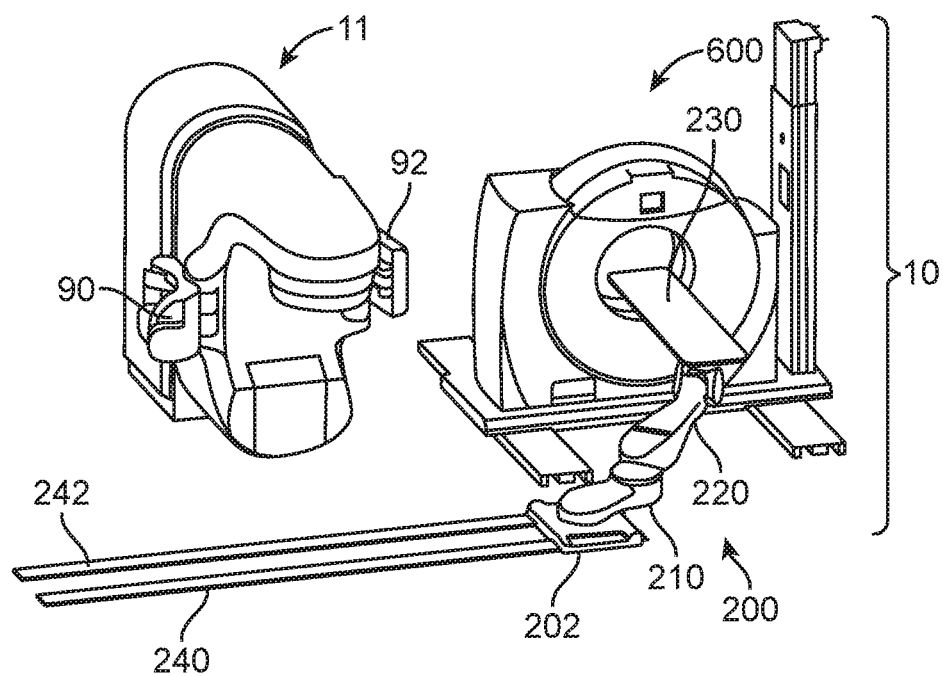
FIG. 6A illustrates a medical system having a treatment machine, an imaging machine, and a patient supporting device.

In any of the embodiments described herein, the treatment system may optionally further include an imaging machine located next to the treatment machine 11. FIG. 6A illustrates an example in which the treatment system includes an imaging machine 600 placed next to the treatment machine 11 in a side-by-side configuration. By means of non-limiting examples, the imaging machine 600 may be a CT machine, a x-ray machine, a fluoroscope, a MRI machine, an ultrasound device, a PET machine, a SPECT machine, or a PET-CT machine. In the side-by-side configuration, both a front of the treatment machine 11 and a front of the imaging machine 600 are facing the same direction. During use, the patient supporting device 200 may be configured to place the patient at a treatment position with respect to the treatment machine 11, and also at an imaging position with respect to the imaging machine 600. For example, before a treatment session begins, the patient supporting device 200 may place the patient at the imaging position to allow the imaging machine 600 to image the patient. The image(s) from the imaging machine 600 may be used to confirm the position and shape of target (e.g., tumorous tissue), and/or be used to perform patient setup. After the image(s) is obtained, the patient supporting device 200 may then move the patient from the imaging position to the treatment position, to thereby allow the treatment machine 11 to deliver treatment energies towards the patient. During treatment, if desired, the patient supporting device 200 may move the patient from the treatment position to the image position to allow the imaging machine 600 to obtain additional image(s) of the patient. The additional image(s) may be used to determine position and/or shape of target, which in turn, may be used to update or modify a treatment plan.

In some embodiments, the patient supporting device 200 may be configured to make motions in multiple different coordinate systems corresponding with respective different machines. For example, the control of the patient supporting device 200 may be configured to operate the patient supporting device 200 to move in a first path within a first coordinate system (e.g., one for the treatment machine 11), and to operate the patient supporting device 200 to move in a second path different from the first path within a second coordinate system (e.g., one for the imaging machine 600).

Figure 6B:
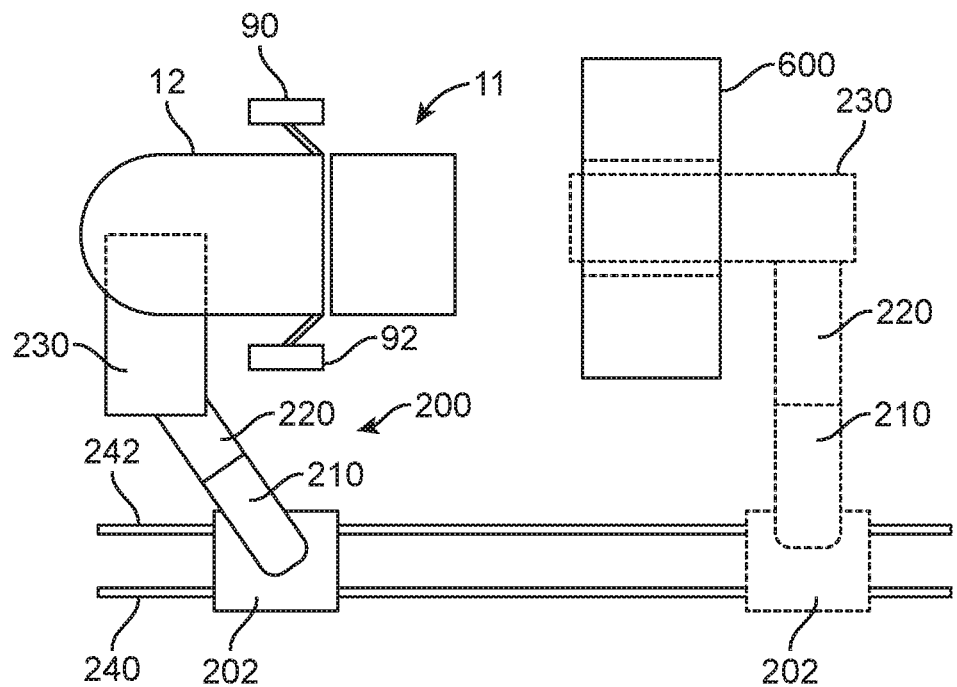
FIG. 6B illustrates another medical system having a treatment machine, an imaging machine, and a patient supporting device.
Figure 6C:
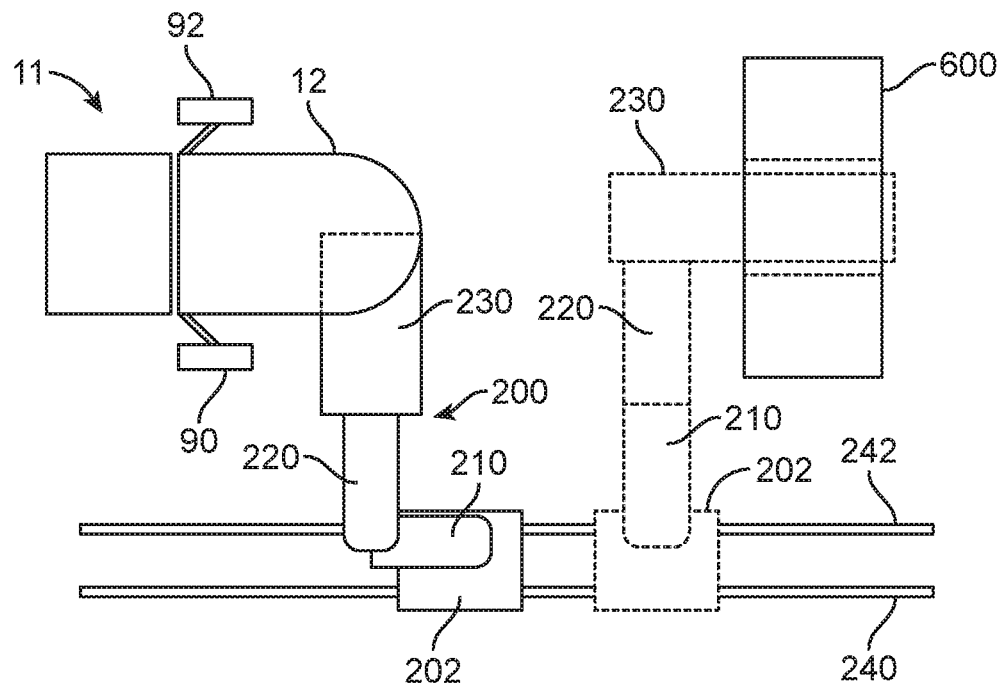
FIG. 6C illustrates another medical system having a treatment machine, an imaging machine, and a patient supporting device.
Figure 6D:
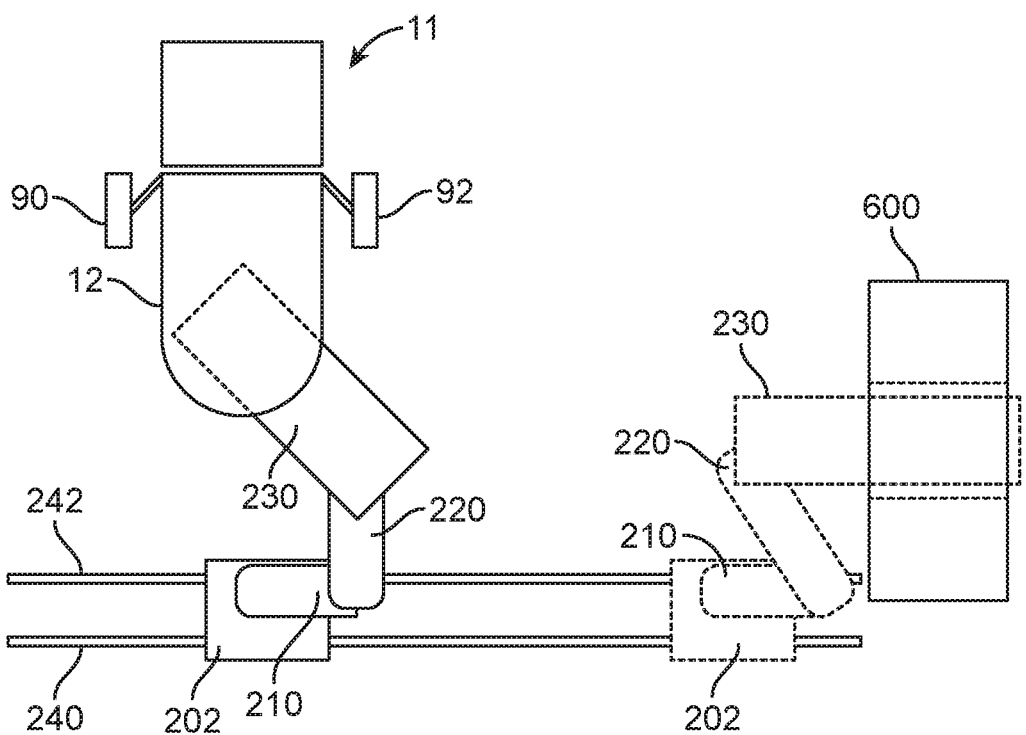
FIG. 6D illustrates another medical system having a treatment machine, an imaging machine, and a patient supporting device.

In other embodiments, instead of the side-by-side configuration, the treatment machine 11 and the imaging machine 600 may be placed next to each other in a back-to-back configuration (in which the back of the treatment machine 11 faces towards the back of the imaging machine 600) (FIG. 6B), or in a front-to-front configuration (in which the front of the treatment machine 11 faces towards the front of the imaging machine 600) (FIG. 6C). In further embodiments, the treatment machine 11 and the imaging machine 600 may be placed next to each other at 90° (or other angles) with respect to each other (FIG. 6D).

In any of the embodiments described herein, the operation of the patient supporting device 200 may be achieved using a control that generates control signals for causing one or more of the components (e.g., base 202, first member 210, second member 220, platform 230) of the patient supporting device 200 to move. The control may include circuitry and/or algorithm for generating the control signals. In some cases, the control may include a processing unit configured to receive and process a treatment plan, which prescribes the condition and/or the manner for moving the platform 230. The processing unit may generate the control signals based on parameters provided from the treatment plan. For example, the treatment plan may include parameters for indicating that the platform 230 be moved from position X to position Y when certain criteria are met. The criteria may be a position of the energy output of the treatment machine 11, a total accumulated dose delivered to the patient, an amount of dose delivered to target, an amount of dose delivered to critical organ, etc. In some embodiments, the control for the patient supporting device 200 may include a member control module for controlling movement of the first member 210 and/or the second member, a base control module for controlling a movement of the base 202, and a platform control module for controlling a movement of the platform 230 relative to the second member 220. Also, in some embodiments, the treatment plan may prescribe the positions and orientations of the platform 230 to be accomplished at certain time points or certain conditions, and the control of the patient supporting device 200 may include an analysis module configured to determine which component(s) (e.g., the base 202, the first member 210, the second member 220, the platform 230) to move and amount(s) of movement to accomplish the prescribed positions and orientations of the platform 230.

Also, in the above embodiments, the rails 240, 242 are described as being at the floor (e.g., they can be mounted on or in the floor). In other embodiments, the rails 240, 242 may be mounted at the ceiling of the operating room. In further embodiments, the rails 240, 242 may be mounted to a wall of the operating room. Regardless of where the rails are mounted, the base 202 is configured to translate (e.g., in a rectilinear path, in a curvilinear path, or both) within a room. Furthermore, instead of two rails, in other embodiments, the base 202 may be configured to move along only one rail, or more than two rails. In still further embodiments, the rails 240, 242 may not be required. For example, in other embodiments, the base 202 may include one or more wheels for allowing the base 202 to move in a room. In some cases, the base 202 may have multiple wheels and the base 202 is steerable. Also, in some embodiments, the moveable base 202 may allow the patient supporting device to be transported outside the treatment room into a hallway and/or to another room.

In addition, in other embodiments, instead of defining the path of the base 202 using rail(s), the base 202 may include wheels and the positioning of the base 202 may be accomplished by turning and/or steering the wheels. In one implementation, the base 202 may include omni-directional wheels. In other embodiments, the base 202 may include other types of wheels, such as tractor-type wheels.

In any of the embodiments described herein, the patient supporting device 200 may also include a control for allowing an operator to enter one or more commands to control a positioning and/or a movement of the platform 230. For example, in some cases, the control may include a keyboard and/or a mouse for allowing a user to prescribe a coordinate and/or an orientation for the platform 230. In response to the command(s) entered by the operator, a processing unit may then operate the platform 230, the first member 210, the second member 220, the base 202, or any combination of the foregoing, in order to place the platform 230 at the prescribed coordinate and/or orientation. As another example, the control may include a control-stick. In such cases, in response to the operator operating the control-stick in a certain direction (e.g., left, right, forward, backward), the platform 230 will move in the corresponding direction. In some embodiments, the control-stick may also include an up-button and a down-button for moving the platform 230 upward and downward, respectively. Furthermore, in some cases, the user-operable control may be implemented using an iphone, an ipad, a tablet, a laptop, or any of other communication devices. In some embodiments, the control may be in the same room with the patient supporting device 200. In other embodiments, the control and the patient supporting device 200 may be in separate respective rooms. Also, the control may be implemented at the patient supporting device 200, and may be a part of the patient supporting device 200. Furthermore, the control may have a first control interface (e.g., keyboard, mouse, screen, touch-screen, buttons, joystick, or any combination of the foregoing) at the patient supporting device 200, and a second control interface (e.g., keyboard, mouse, screen, touch-screen, buttons, joystick, or any combination of the foregoing) in a room that is different from the room in which the platform 230 is located. In such cases, an operator may selectively choose which of the control interfaces to use for controlling the positioning and/or the movement of the platform 230.

It should be noted that as used in this specification, the term "vertical" refers to an orientation that is approximately 90° (e.g., 90°±10°, and more preferably 90°±5°) with respect to a horizon or a horizontal floor. Also, as used in this specification, the term "horizontal" refers to an orientation that is approximately parallel (e.g., at 0°±10°, and more preferably 0°±5°) to a horizon or a horizontal floor.

Imaging Waypoints

In some embodiments, during a treatment session to treat the patient 28 using the treatment system 10, one or more imaging process to obtain one or more images may be performed. For example, during a treatment session, and between deliveries of treatment energies towards the patient 28, an imaging device may be operated to obtain one or more images of the patient 28. The imaging device may be an imaging source (e.g., radiation source) coupled to the treatment machine 11, a portal imager, or a separate imaging machine (such as an ultrasound machine, a MRI machine, a x-ray machine, a CT machine, etc.). The obtained image(s) may be used to confirm a position of a target region inside the patient 28, to confirm a delivered dose to the patient 28, to adjust a position of the patient 28, to adjust a treatment plan, or any combination of the foregoing.

In accordance with some embodiments, imaging waypoints may be defined and may be incorporated as a part of a treatment plan. As used in this specification, an imaging waypoint may refer to an imaging position for obtaining one or more images, wherein the imaging position may be an image energy source position (e.g., a position of a gantry or an arm carrying an energy source for imaging,), a gantry of a treatment energy source, a position of the patient support 14, an orientation of the patient support 14, etc., or any combination of the foregoing. Accordingly, by means of non-limiting examples, the imaging waypoint data may define a gantry position (e.g., gantry of imaging source and/or treatment source), a couch (patient support) position, a couch orientation, an image energy source position (e.g., as defined by a gantry carrying the imaging energy source), or any combination of the foregoing, for obtaining one or more of the images of the patient 28. In some embodiments, an imaging waypoint may be determined or expressed with respect to a plane within which an imaging energy source is rotated, with respect to a position and/or orientation of the patient support 14, or with respect to both. Also, because one or more components (e.g., gantry, energy source, patient support 14, etc.) involved during a medical procedure may have positions that are associated with respective time points, in some cases, imaging waypoints may refer to, represent, and/or associated with, those points in time where imaging is possible. An imaging waypoint, in some embodiments, may represent an instantaneous temporal opportunity to acquire image(s) or a time slot where images can be acquired over a period of time. Imaging based on imaging waypoints may be in parallel or sequential with respect to treatment beam delivery.

In some embodiments, imaging waypoints may be defined before determining beam-on directions (treatment trajectories). A beam-on direction is the direction of treatment energy provided by a treatment energy source. In some cases, a beam-on direction may be at least partially defined by determining a gantry angle (i.e., an angle of the gantry carrying a treatment energy source) at which treatment energy is to be delivered. In some embodiments, the beam-on direction(s) may be at least partially defined with respect to a plane within which the treatment energy source is rotated, with respect to a position and/or orientation of the patient support 14, or with respect to both. Defining imaging waypoints before beam-on directions are determined may be beneficial if a specific feature in the patient 28 is visible from a specific direction using a specific imaging method. For example 3D cone beam (CB) CT quality may depend on arc length (angle). If full rotation or a partial rotation for a CBCT image is desired, it may be set in advance using imaging waypoints. In another example, tumor may be visible from a specific angle. In this case the imaging direction may be set in advance. In one example, a lung tumor may be best visible from gantry angle=0°. As such, in this example, imaging waypoint(s) may be set at gantry angle=0°, or a range of imaging waypoints may be set at gantry angle range=10° to 10° for allowing such imaging to be performed.

Figure 11A:
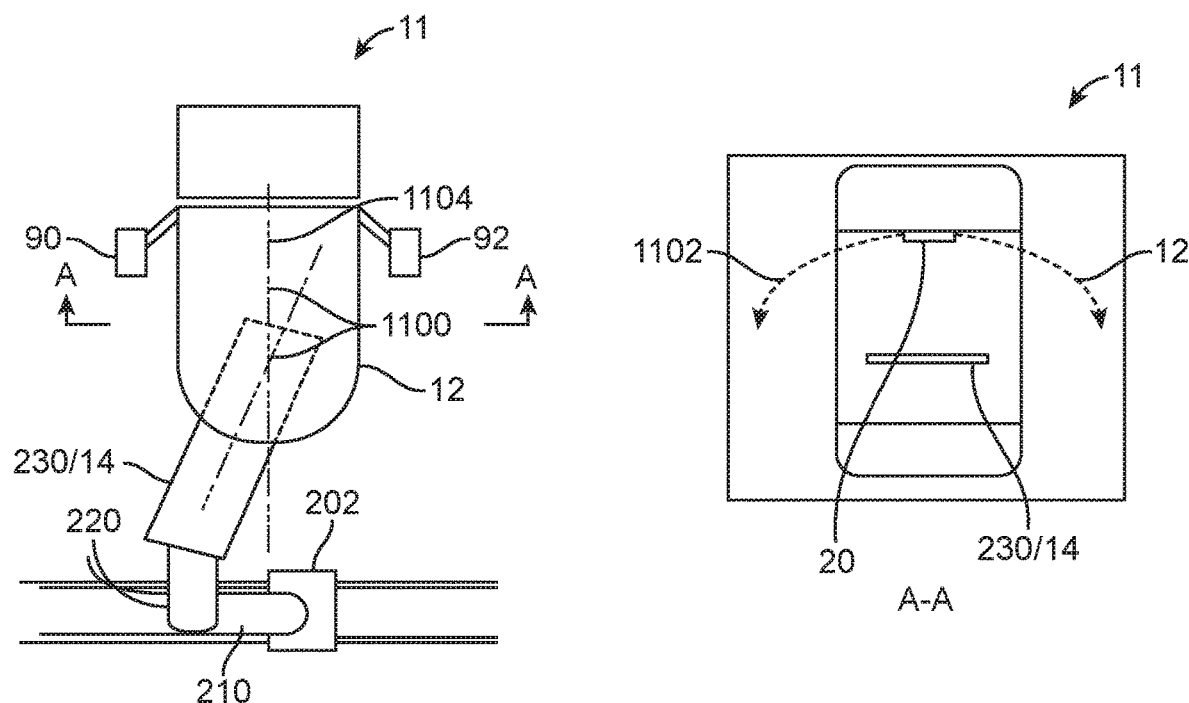
FIG. 11A illustrates an example of an orientation and position of a patient support relative to a treatment machine.

After imaging waypoints are determined, beam-on directions may then be determined. In some cases, the imaging waypoints may be taken into consideration when determining the beam-on directions. For example, if a patient support angle 1100 of 25° (which is an example of an imaging waypoint) is used for imaging, such orientation of the patient support 14 may also be used while delivering treatment energy from different gantry angles (FIG. 11A). This way, full treatment delivery may be performed without moving the patient support 14 between imaging position and treatment position (e.g., without rotating patient support 14 about a vertical axis in the above example to another position for treatment), thereby reducing the risk of patient movement. As shown in FIG. 11A, the angle 1100 of the patient support 14 is measured relative to an arbitrary axis 1104, and the angle 1100 is within a plane (e.g., a horizontal plane) that forms an angle (e.g., a 90° angle) relative to a rotational plane of the gantry 12/treatment source 20. The rotational plane of the gantry 12/treatment source 20 is the plane in which the gantry 12/treatment source 20 rotates (as represented by arrow 1102).

In another cases, a user may select (through a user interface) a certain type of imaging with the patient support 14 at an angle 1100 of 5° (wherein the angle 1100 is within a horizontal plane and is with respect to a certain horizontal axis). For example, the user may select kV-MV pair imaging (i.e., imaging using kV energy and MV energy to obtain a pair of images) to be performed while the patient support 14 is at the angle 1100 of 5°. The user may also choose a certain type of treatment technique. For example, the user may choose Rapid Arc treatment (available at Varian, Palo Alto). The apparatus may then determine beam-on directions and imaging direction(s) based on the orientation of the patient support 14 being at 5°. Continuing with the above example, the apparatus may (based on the patient support angle 1100 of 5°, position, size, and/or shape of target region in the patient) determine a treatment plan with beam-on directions being from a range of gantry angles of 35° to 85°, and imaging directions being from a range of imaging angles from 25° to 40°.

In other embodiments, the apparatus may automatically determine imaging waypoints and beam-on directions based on user defined parameters. For example, a user may choose KV-MV pair at patient support angle 1100 of 5° (an example of imaging waypoint) and RapidArc treatment with full gantry rotation while the patient support angle is at 0°. The apparatus may then create a treatment plan that contains (1) imaging while patient support 14 is at angle 1100 of 5°, and (2) full rotation arc for treatment while the patient support 14 is at angle 1100 of 0°.

In other embodiments, imaging waypoints may be defined after the beam-on trajectory definition. In some cases, after the beam-on trajectories are determined, an apparatus may be provided for proposing directions where imaging is possible. For example, it may be the case that a user selects a full rotation arc for treatment while the isocenter remains in the patient 28. Based on the selection of full rotation arc treatment, and other information (such as the position, size, and/or shape of structures inside the patient 28), the apparatus may determine that imaging is possible at each point along the treatment arc. The user may then choose any location of along the treatment arc to for planned imaging.

In another example, the user may select partial arc treatment with off-center isocenter. In this example, beam-on directions for the partial arc treatment is from gantry angles of 0°-180°. Based on this information, and other information (such as the position, size, and/or shape of structures inside the patient 28), the apparatus may determine that imaging without moving isocenter or patient support 14 is possible only at gantry angles 0°-67°. Accordingly, the apparatus may allow the user to set imaging waypoints for planned imaging in this range.

As a further example, a user may select partial arc treatment with off-center isocenter. In such cases, the partial arc treatment involves a gantry rotation from 0°-180°. The apparatus may determine that imaging without moving isocenter or the patient support 14 is possible only at gantry angles of 0° to 67°. However, user may want to image from angle 90°. The apparatus may then notify that this requires an isocenter shift or a movement of the patient support 14. The apparatus may create a treatment plan having both planned imaging and planned treatment with an isocenter shift. For example, the apparatus may determine that the partial arc treatment is to be performed with the patient support 14 being at angle 1100 of 15°, and planned imaging is to be performed with the patient support being at angle 1100 of 45°.

In further embodiments, the imaging waypoints may be defined as a class solution. In such cases, a sub-set of possible schemes (e.g., treatment schemes and/or imaging schemes) may be parametrized and proposed to a user. The sub-set of possible schemes may be designed for low collision risk, good imaging capabilities, and/or any of other treatment considerations.

Figure 11B:
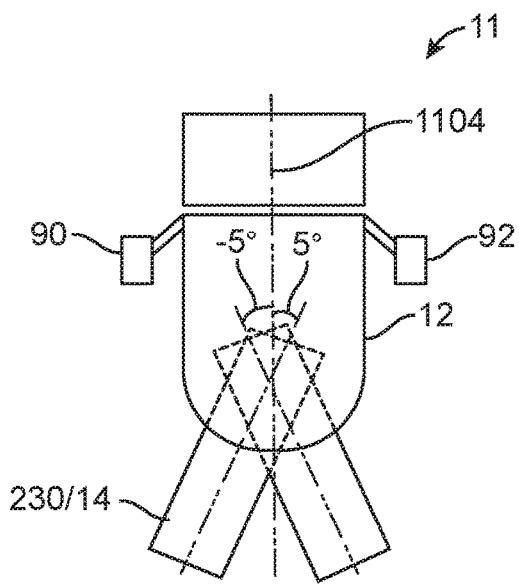
FIG. 11B illustrates an example of allowable range of rotation of a patient support relative to a treatment machine.

For example, a user interface may be provided that allows a user to select half-arc CBCT imaging (gantry from 0 to 180 degrees) with an envelope of allowed isocenter locations. The envelope of allowed isocenter locations may be defined so that half-arc CBCT is possible. In this example, the user may select the half-arc CBCT imaging as a class solution. After the class solution is selected, the user may also choose, through the user interface, an isocenter location in the allowed range as defined by the envelope. In other embodiments, the user may choose a full-arc CBCT imaging as a class solution. In further embodiments, half-arc or full-arc CBCT imaging may be selected as a class action with corresponding envelope of allowed isocenter locations, and also with allowable range of patient support rotation (e.g., allowable angle 1100 may be anywhere from −5° to 5°; see FIG. 11B).

Figure 7:
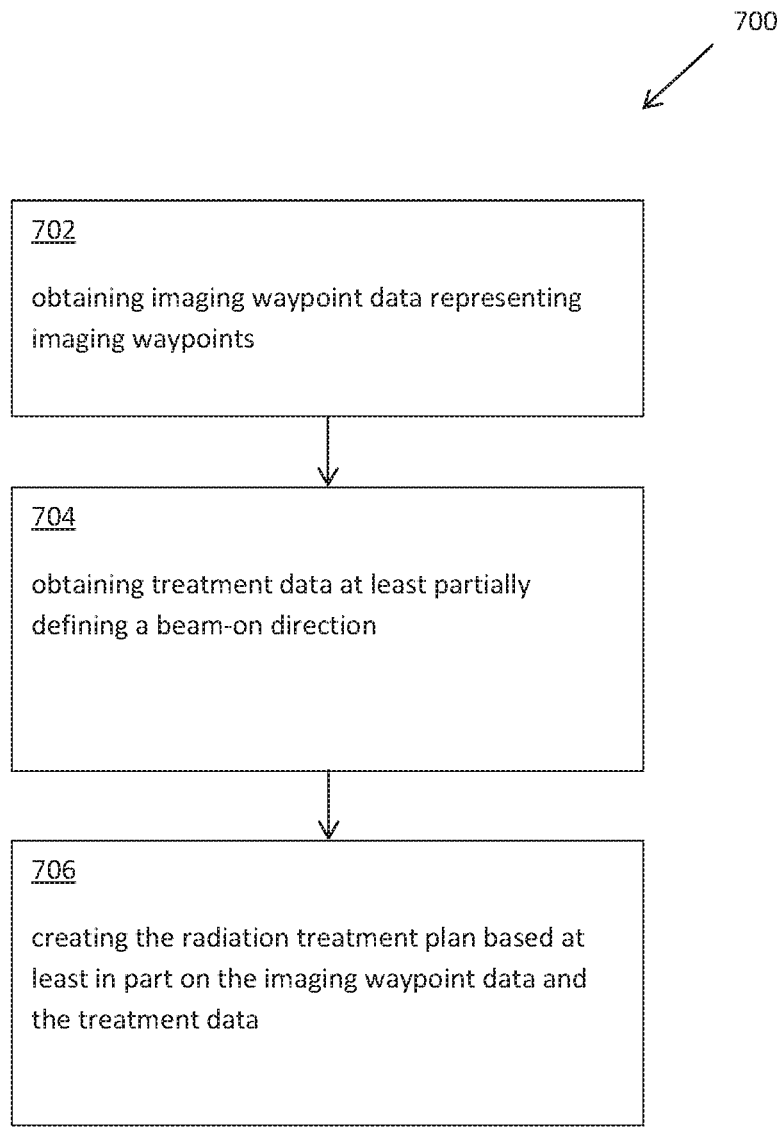
FIG. 7 illustrates a method for creating a treatment plan.

FIG. 7 illustrates a method 700 for creating a radiation treatment plan for execution by a radiation treatment machine in accordance with some embodiments. The method 700 includes obtaining imaging waypoint data representing imaging waypoints (item 702), wherein the imaging waypoints at least partially define one or more positions for obtaining images of a patient. By means of non-limiting examples, the imaging waypoint data may define a couch position, a couch orientation, an image energy source position, or any combination of the foregoing, for obtaining one or more of the images of the patient. In one specific example, the imaging waypoint data may be an orientation of the patient support 14 with respect to a treatment machine 11, such as the angle 1100 shown in FIG. 11.

In some embodiments, the act of obtaining the imaging waypoint data may be performed by an input of an apparatus, which receives the imaging waypoint data (e.g., from another device, or from a user interface). In other embodiments, the act of obtaining the imaging waypoint data may be performed by an apparatus, which retrieves the imaging waypoint data from a non-transitory medium. The non-transitory medium may be in the apparatus, or may be outside the apparatus that is in communication with the apparatus.

Returning to FIG. 7, the method 700 also includes obtaining treatment data at least partially defining a beam-on direction (item 704). By means of non-limiting examples, the treatment data may define a gantry angle or a range of gantry angles for an energy source to deliver treatment energies. In some cases, the treatment data may define a couch position, a couch orientation, a treatment energy source position, or any combination of the foregoing, for delivering one or more treatment energies to the patient. For example, the treatment data may indicate that treatment is to be performed with the patient support 14 being at a certain orientation and position with respect to the treatment machine 11.

In some embodiments, the act of obtaining the treatment data may be performed by an input of an apparatus, which receives the treatment data (e.g., from another device, or from a user interface). In other embodiments, the act of obtaining the treatment data may be performed by an apparatus, which retrieves the treatment data from a non-transitory medium. The non-transitory medium may be in the apparatus, or may be outside the apparatus that is in communication with the apparatus.

The method 700 also includes creating the radiation treatment plan based at least in part on the imaging waypoint data and the treatment data (item 706). In some embodiments, the created treatment plan includes treatment scheme and imaging scheme that are integrated with each other. For example, the treatment plan may prescribe that treatment energy be delivered while the patient support 14 is at an angle 1100 that is 0°, with the treatment energy source rotating from gantry angle of −30° to 45° to deliver treatment energies in this range. After the treatment energy is delivered, the treatment plan may prescribe that the patient support 14 be rotated so that the angle 1100 is 10°. At that position, the treatment plan may prescribe that imaging be performed on the patient 26, and that the energy source be rotated from gantry angle of −50° to 60° to deliver treatment energies in this range. In some cases, the prescribed positional relationship between the patient support 14 and the treatment machine 11 for the various items in the operational sequence may be stored in a specialized data structure as a part of the treatment plan. During use, the data structure is executable or operable by a processing unit to thereby cause the items in the operational sequence to be performed.

In some embodiments, the imaging waypoint data may be obtained before the treatment data is obtained. In such cases, after the imaging waypoint data is obtained, the treatment data may be obtained based on the imaging waypoint data. Also, in some embodiments, the imaging waypoint data may comprise a user input indicating a desired position for imaging. In such cases, the treatment data may be obtained based on the user input. In other embodiments, the treatment data may be obtained before the imaging waypoint data is obtained.

In some cases, the method 700 may further include generating proposed directions where imaging is possible based on the treatment data, wherein the imaging waypoint data is obtained based on the proposed directions. The method 700 may further include receiving a user input indicating a selected one of the directions, wherein the imaging waypoint data is obtained based on the user input.

Optionally, the method 700 may further include determining a set of possible schemes for imaging and/or treatment. In some cases, the set of possible schemes may be determined based on collision avoidance, imaging capability, or both. The method 700 may further include receiving a user input representing a selected one or more of the possible schemes.

Figure 8:
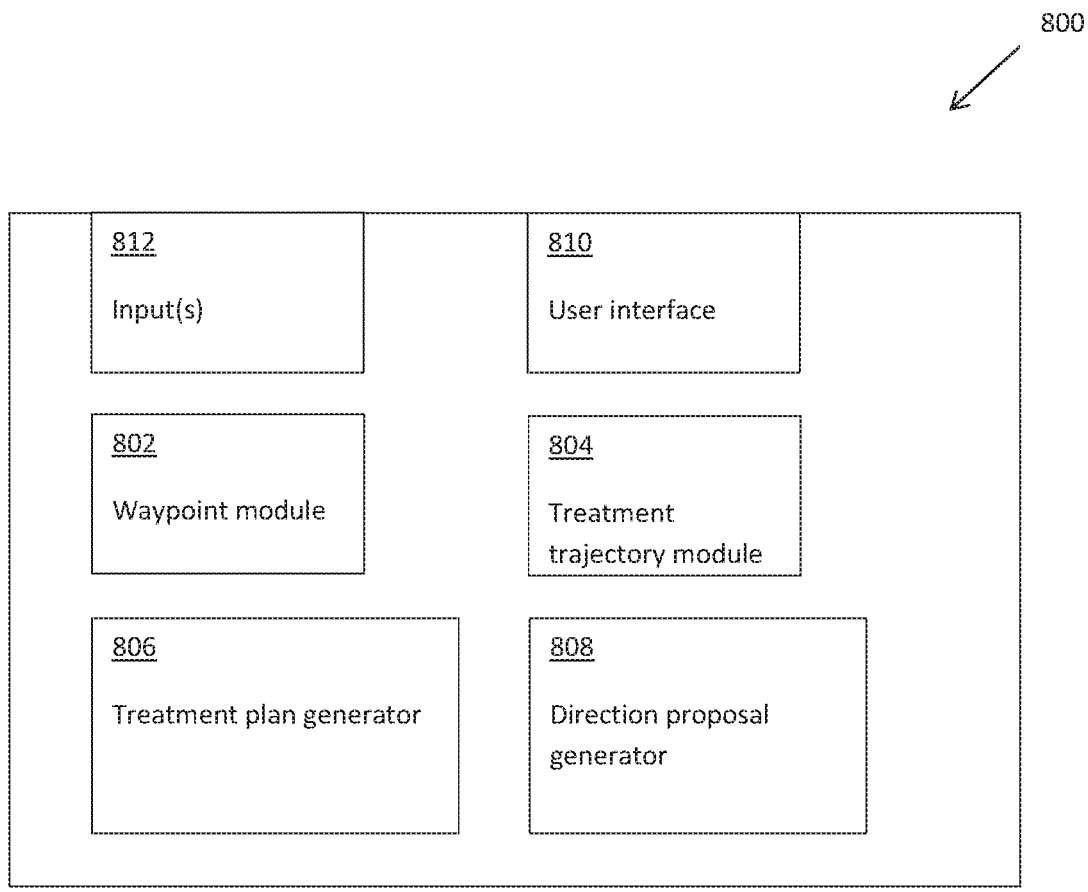
FIG. 8 illustrates an apparatus for creating a treatment plan.

FIG. 8 illustrates an apparatus 800 for creating a radiation treatment plan for execution by a radiation treatment machine. In some cases, the apparatus 800 may be used to perform the method 700 of FIG. 7. Referring to FIG. 8, the apparatus 800 include: a waypoint module 802 configured to obtain imaging waypoint data representing imaging waypoints, the imaging waypoints at least partially defining one or more positions for obtaining images of a patient during a treatment session. The apparatus 800 also includes a treatment trajectory module 804 configured to obtain treatment data at least partially defining a beam-on trajectory, and a treatment plan generator 806 configured to create the radiation treatment plan based at least in part on the imaging waypoint data and the treatment data.

In some embodiments, the imaging waypoint data may define a couch position, a couch orientation, an image energy source position, or any combination of the foregoing, for obtaining one or more of the images of the patient 28.

Also, in some embodiments, the treatment data may define a gantry angle or a range of gantry angles for an energy source to deliver treatment energies. In some cases, the treatment data may define a couch position, a couch orientation, a treatment energy source position, or any combination of the foregoing, for delivering one or more treatment energies to the patient. For example, the treatment data may indicate that treatment is to be performed with the patient support 14 being at a certain orientation and position with respect to the treatment machine 11.

In some embodiments, the waypoint module 802 may be configured to obtain the imaging waypoint data before the trajectory module 804 obtains the treatment data. Also, in some cases, the treatment trajectory module 804 may be configured to obtain the treatment data based on the imaging waypoint data. In addition, in some cases, the imaging waypoint data comprises a user input indicating a desired position for imaging, wherein the treatment trajectory module 804 may be configured to obtain the treatment data based on the user input. In other embodiments, the treatment trajectory module 804 may be configured to obtain the treatment data before the waypoint module 802 obtains the imaging waypoint data.

Also, in some embodiments, the apparatus 800 further includes a direction proposal generator 808 configured to generate proposed directions where imaging is possible based on the treatment data, wherein the waypoint module 802 is configured to obtain the imaging waypoint data based on one or more of the proposed directions. For example, the treatment data may indicate that treatment is to be delivered while the patient support 14 is at a certain orientation with respect to the treatment machine 11. Based on such information, and information regarding a position, size, and/or shape of structure(s) in the patient 26, the direction proposal generator 808 may propose that imaging be performed at imaging angle from 30° to 55°, for example. In some cases, the direction proposal generator 808 may also propose that the position and/or orientation of the patient support 14 relative to the treatment machine 11 be varied from the treatment position for imaging. In some cases, the apparatus 800 may further include a user interface 810 configured to receive a user input indicating a selected one of the directions, wherein the waypoint module 802 is configured to obtain the imaging waypoint data based on the user input.

In some embodiments, the treatment trajectory module 804 may also be configured to determine a set of possible schemes for treatment and/or imaging. For example, the treatment trajectory module 804 may be configured to determine the set of possible schemes based on collision avoidance, imaging capability, or both. Optionally, the apparatus 800 may further include a user interface 810 for receiving a user input representing a selected one or more of the possible trajectories.

As shown in FIG. 8, in some embodiments described herein, the apparatus 800 may further include one or more input(s) 812 for receiving information, such as treatment plan parameters, medical images (e.g., projection images, CT image, ultrasound image, PET image, SPECT image, PET-CT image, SPECT-CT image, x-ray, MRI image, etc.), machine model(s) (e.g., model of treatment machine, model of patient supporting device, etc.), or any combination of the foregoing.

It should be noted that the method 700 and the apparatus 800 are advantageous because they allow a user to integrate treatment trajectories with imaging, while considering the type of treatment and the type of imaging, and the geometry of the patient (e.g., locations, sizes, and/or shapes of the target region and surrounding organs). The method 700 and the apparatus 800 also provide immediate feedback, input, and/or suggestion (regarding possible treatment trajectories) for treatment planning, in response to a user's selection of imaging waypoints. The method 700 and the apparatus 800 also may alternatively provide immediate feedback, input, and/or suggestion (regarding possible imaging scheme) for treatment planning, in response to a user's selection of treatment trajectories. The method 700 and the apparatus 800 are technological improvements over existing treatment planning devices and methods because it is believed that existing treatment planning devices and methods do not involve the intelligence and processing functions provided in embodiments of the method 700 and apparatus 800.

Furthermore, the apparatus 800 may be configured to determine at what machine states (e.g., angles) it is safe to deploy an imager (e.g., a kV imager) and to acquire image(s). By means of non-limiting example, allowable machine states for acquiring image(s) may include: the deployment state of the kV imager, such as an angle of the arm carrying the imager, the deployment state of an imaging source, etc. Accordingly, imager may be deployed "on the fly" during a treatment session.

In addition, in some embodiments, the apparatus 800 may be configured to determine where images have been successfully acquired in previous similar treatments. For example, the apparatus 800 may include an input for receiving information regarding how previous images were obtained (e.g., where was the imaging source, and/or the imager, etc.). In another example, the apparatus 800 may be configured to track previous imaging configurations, and store information about those imaging configurations in a non-transitory medium. The information may then be later used by the apparatus 800 to determine quickly whether imaging is possible at a certain machine configuration during treatment session. The information may also be used by the apparatus 800 to quickly determine a treatment plan that includes imaging consideration.

Partial Treatment Consideration

Sometimes treatment may be interrupted before full radiation dose for the specific fraction is delivered. For example, if the patient 28 is sick and vomits during a treatment session, the treatment may be interrupted. After clinical evaluation, the treatment may be later continued to deliver the remaining planned dose in the fraction, to deliver the remaining dose in a new fraction, or to deliver a completely re-planned dose.

In some cases, component(s) of the treatment machine 11, the patient supporting device 200, component(s) of the imaging device 90/92/600, or any combination of the foregoing, may be in positions where patient unloading is difficult or impossible. For example, if the patient supporting device 200 is at a very high position, it may be difficult to unload the patient 28 when the treatment is interrupted. As another example, an arm carrying a treatment radiation source 20 and/or an imaging source may be below the patient support 14 so that lowering of the patient support 14 cannot be achieved to unload the patient 28.

Similar problem exists for loading the patient 28 when continuing a treatment that has been interrupted. Decision may be made that the remaining dose is to be delivered to the patient 28. In such cases, the patient 28 may be loaded onto the patient support 14 in a safe loading position. For example, the patient support 14 should be at an elevation that is not too high so as to allow the patient 28 to be placed, or to get, on the patient support 14. The patient support 14 should also be at a position relative to other components (e.g., gantry 12 of the treatment machine 11, component of imaging device 90/92/600, etc.), so that when the patient 28 is being loaded onto the patient support 14, the patient 28 will not collide with any of those components. After the patient 28 is loaded onto the patient support 14, the patient supporting device 200 may then be operated to position the patient support 14 at a location where the treatment can be continued.

Sometimes, it may be desirable to perform an imaging (e.g., cone beam CT imaging) before continuing the treatment. In such cases, the patient 28 may be loaded when the patient support 14 is at safe loading position. The patient supporting device 200 may then be operated to move the patient support 14 to an imaging position (e.g., imaging position associated with the imaging device 600) for performing imaging. After the imaging is performed, the patient supporting device 200 may then be operated to move the patient support 14 to a treatment position (e.g., treatment position associated with the treatment machine 11) where treatment energy may be delivered to the patient 28.

In some embodiments, one or more components of the treatment system 10 may be operated to position the patient support 14 to a safe patient loading or unloading position. For example, the gantry 12 of the treatment machine 11, and/or a component of an imaging device (e.g., device 90, 92, or 600), may need to be moved out of the way, so that patient support 14 can be lowered. In some cases, it may not be easy to quickly figure out how the various components involved in the treatment process should be moved so that the patient support 14 can reach a safe loading or unloading position. Accordingly, in accordance with some embodiments, the treatment system 10 may include an apparatus (e.g., control) configured to automatically operate one or more of the components (e.g., component(s) of the treatment machine 11, component(s) of an imaging device 90/92/600, component(s) of the patient supporting device 200, or any combination of the foregoing) to move the patient support 14 to a safe patient loading or unloading position.

In some cases, when treatment is interrupted, and the operation of the treatment machine 11 and the patient supporting device 200 is stopped, the components of the treatment machine 11, components of an imaging device, and the components (including the patient support 14) of the patient supporting device 200 are at certain positions. Given a desired unloading position for the patient support 14 to be achieved for unloading the patient, there may be many ways to operate the treatment machine 11, imaging device, and the patient supporting device 200 in order to move the patient support 14 from the initial position (when the treatment is interrupted) to the desired position (for unloading the patient 28).

In some embodiments, an apparatus is provided to determine a sequence of operations to control components of the treatment machine 11, components of an imaging device, and the patient supporting device 200 in order to move the patient support 14 from an initial position to a desired final position. In one implementation, the apparatus may employ a shortest path algorithm (such as A* or Dijkstra algorithm) to determine which component(s) to move, amount(s) of movement(s), and a sequence (order) of the movement(s) of the component(s). The apparatus may be configured to receive an initial set of coordinates, which are the current coordinates of the various moveable components (e.g., the gantry, arm, patient support 14, etc.). The initial set of coordinates may be the positions of the various components when the treatment session is interrupted. In some cases, the initial set of coordinates includes the position of the patient support 14 when the treatment is stopped. The apparatus may also receive a final desired position of the patient support 14 to be achieved for unloading the patient. The apparatus utilizes the shortest path algorithm to determine how to move the component(s) to transfer the patient support 14 from the current position to the desired position (a safe location) for unloading the patient.

Similarly, in another mode of operation, the initial set of coordinates may be the positions of the various components when the patient support 14 is at a safe position for loading the patient 28. In such cases, the apparatus may receive a desired set of coordinates of the various components to be achieved, which may include a desired position of the patient support 14, for delivering treatment energy to the patient 28. The apparatus utilizes the shortest path algorithm to determine how to move the component(s) to transfer the patient support 14 from the current position (loading position) to the desired position (treatment position) for treating the patient. For example, when treatment was interrupted, the gantry 12 may be at 48° angle, and the patient support 14 may be at position (x=34, y=62, z=50, θx=36°, θy=0°, θz=0°). To unload the patient 28, the gantry 12 may be moved to 0° angle, and the patient support 14 may be moved to position (x=12, y=30, z=100, θx=90°, θy=0°, θz=0°). To resume treatment, the patient 28 may be loaded back to the patient support 14, and the apparatus then determines a sequence of actions to move the patient support 14 back to the treatment position (which, in the above example, is x=34, y=62, z=50, θx=36°, θy=0°, θz=0°). The sequence of actions in the above example will also involve moving the gantry 12 from 0° angle back to 48° angle.

In other embodiments, instead of utilizing a shortest path algorithm, the apparatus may obtain a predetermined sequence of actions to be performed for moving the patient support 14 from an initial position to a desired position. For example, the predetermined sequence of actions may be:

1) Retract imaging arms
2) Rotate gantry 12 to the 0° angle
3) lower the patient support 14 to a prescribed elevation.

Figure 9:
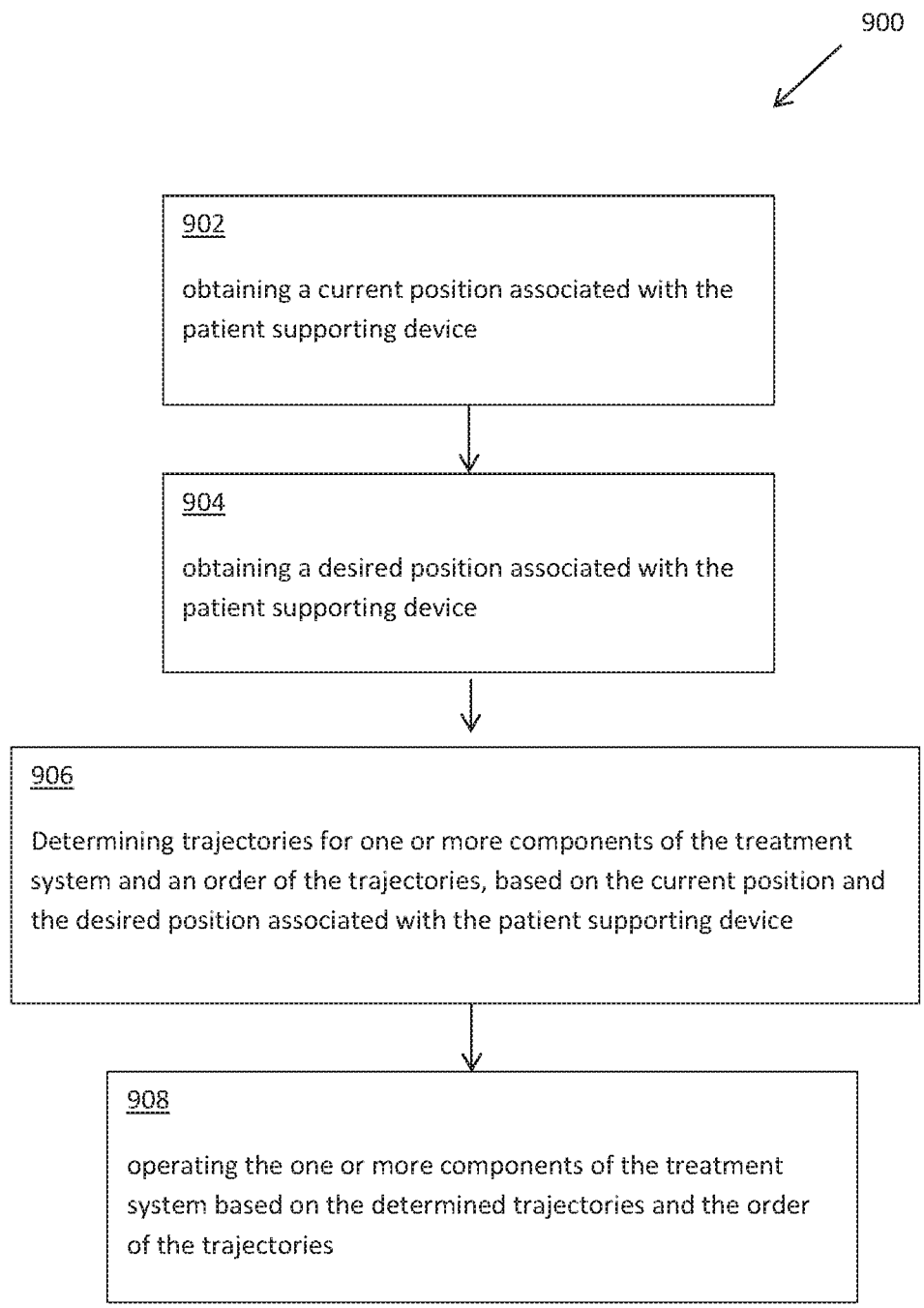
FIG. 9 illustrates a method of operating a medical system.

FIG. 9 illustrates a method 900 of operating a medical system in accordance with some embodiments. The medical system includes a treatment machine and a patient supporting device, such as the example shown in FIG. 1. The method 900 may be performed by an apparatus configured to move the patient support 14 from an initial position to a desired position. The method 900 of FIG. 9 includes obtaining a current position associated with the patient supporting device 200 (item 902). In some embodiments, the current position may be the position of the patient support 14 when a treatment is interrupted. In other embodiments, the current position associated with the patient supporting device 200 may be the position of the patient support 14 when the patient 28 is being loaded at a safe location. In other embodiments, the current position may be one or more coordinates of one or more respective components of the patient supporting device 200, when treatment is stopped (e.g., interrupted), or when the patient 28 is being loaded. In further embodiments, the current position may be a position Pp (e.g., with respect to a coordinate system, such as the coordinate system of the treatment machine 11 or the treatment system 10) of a part of the patient 28 that is supported on the patient support 14. The position P1 of the part of the patient 28 relative to a position Ps of the patient support 14 may be known in advance (i.e., Pp=Ps+p1). As such, the part of the patient 28 may be later positioned back to the position Pp by moving the patient support 14 to the position Ps (which is equal to Pp−P1).

Also, in some embodiments, the act of obtaining the current position may be performed by an input of an apparatus, which receives data representative of the current position. The data may be received from a device, which includes a user interface for allowing a user to enter the data. Alternatively, the data may be received from a position sensor or a position indicator, which is configured to determine the current position. It should be noted that as used in this specification, the term "position" may refer to one or more position(s), such as a position of a component of the patient supporting device 200, or multiple positions of different components of the patient supporting device 200.

Referring to FIG. 9, the method 900 also includes obtaining a desired position associated with the patient supporting device 200 to be achieved (item 904). In some embodiments, the desired position may be the position of the patient support 14 when treatment energy may be delivered to the patient 28. In other embodiments, the desired position associated with the patient supporting device 200 may be the position of the patient support 14 when the patient 28 is being loaded or unloaded at a safe location. In other embodiments, the desired position may be one or more coordinates of one or more respective components of the patient supporting device 200, when treatment is resumed, or when the patient 28 is being loaded or unloaded. In further embodiments, the desired position may be a position Pp (e.g., with respect to a coordinate system, such as the coordinate system of the treatment machine 11 or the treatment system 10) of a part of the patient 28 that is supported on the patient support 14. The position P1 of the part of the patient 28 relative to a position Ps of the patient support 14 may be known in advance (i.e., Pp=Ps+p1). As such, the part of the patient 28 may be later positioned to the position Pp by moving the patient support 14 to the position Ps (which is equal to Pp−P1).

Also, in some embodiments, the act of obtaining the desired position may be performed by an input of an apparatus, which receives data representative of the desired position. The data may be received from a device, which includes a user interface for allowing a user to enter the data. Alternatively, the data may be stored in a non-transitory medium. For example, the data may be stored in association with a treatment plan. In such cases, the act of obtaining the desired position may be performed by the apparatus that retrieves the data from the non-transitory medium.

Continuing with FIG. 9, the method 900 further includes determining, by the apparatus (e.g., a trajectory module in the apparatus), trajectories for one or more components of the treatment system 10, and an order of the trajectories, based on the current position and the desired position associated with the patient supporting device 200 (item 906). For example, the apparatus may determine trajectories for the treatment machine 11 and for one or more components of the patient supporting device 200, and an order of the trajectories, based on the current position and the desired position associated with the patient supporting device 200. As used in this specification, the term "trajectory" may refer to a direction of movement for one or more components, an amount of the movement, or both. For example, a trajectory may be a rotation of an arm of the patient supporting device 200 by a certain angular range. As another example, a trajectory may be a translation of the patient support 14 in the x-direction by a certain distance. As a further example, a trajectory may be a rotation of the patient support 14 about a vertical axis by a certain angular range. In still a further example, a trajectory may be a rotation of the gantry 12 of the treatment machine 11 by a certain angular range.

In some cases, the trajectory module determines the trajectories and the order of the trajectories using a shortest-path algorithm. The trajectory module may be configured to obtain one or more parameters for determining the trajectories and the order of the trajectories. By means of non-limiting examples, the parameter(s) may include degrees of freedoms of the various components, movement speeds of the various components, movement constraint(s) of one or more of the components, or any combination of the foregoing. The components may be any of the components in the treatment system 10, such as any of the components of the treatment machine 11, any of the components of the patient positioning device 200, any of the components of an imaging device, or any combination of the foregoing.

Also, in some embodiments, the trajectory module may be configured to perform an optimization to determine the trajectories and the order of the trajectories. The optimization may be performed with respect to one or more optimization objective(s). For example, the trajectory module may be configured to perform the optimization to determine the trajectories and the order of the trajectories that would result in the least amount of time to move the patient support 14 from the initial position to the desired position. As another example, the trajectory module may be configured to perform the optimization to determine the trajectories and the order of the trajectories that would result in the least amount of traveling distance and/or angular motion required by all of the components, or by one or more of the components, to move the patient support 14 from the initial position to the desired position. As another example, the trajectory module may be configured to perform the optimization to determine the trajectories and the order of the trajectories that would result in a reduced or a minimal number of stop-and-go movements for all of the components, or for one or more of the components of the treatment system 10.

In addition, in some embodiments, the trajectory module may be configured to determine whether two or more components of the treatment system 10 may be simultaneously operated to move along two paths without interfering with each other. If so, the trajectory module may prescribe the two or more components be moved simultaneously in the order of the trajectories. Such technique may have the benefit of reducing the time it takes to move the patient support 14 from an initial position to a desired position.

Furthermore, in some embodiments, when performing the optimization, weights may be assigned to different components. For example, it may be desirable to reduce or minimize the amount of time that the patient support 14 moves, and/or the amount of distance to be travelled by the patient support 14. In such cases, the patient support 14 may be assigned a relatively lower weight compared to other components.

After the trajectories for one or more components of the treatment machine 11 and for one or more components of the patient supporting device 200, and an order of the trajectories have been determined, the trajectories and the order of the trajectories may be stored in a non-transitory medium. During use, the apparatus may retrieve the trajectories and the order of the trajectories, and use such information to control movements of the corresponding components.

Referring to FIG. 9, the method 900 also includes operating the one or more components of the treatment system 10 based on the determined trajectories and the order of the trajectories (item 908). For example, the apparatus may generate one or more control signals to operate one or more components of the treatment machine 11 and the one or more components of the patient supporting device 200. In some embodiments, the act of operating the one or more components may include generating one or more control signals for operating the one or more components. The control signal(s) may cause one component to be operated after another component is operated (i.e., in sequence). Alternatively, the control signal(s) may cause two or more components to be operated simultaneously. In further embodiments, the control signal(s) may cause two or more components to be operated simultaneously during a part of an operation sequence, and may cause a component to be operated in sequence after another component is operated during another part of an operation sequence. Furthermore, in some embodiments, the act of operating the one or more components is performed in correspondence with the trajectories and order of the trajectories determined in item 906.

In some cases, the act of operating the one or more components of the treatment machine 11 and the one or more components of the patient supporting device 200 may include moving one of the one or more components of the treatment machine 11 to open up a path for the one or more components of the patient supporting device 200, and moving one of the one or more components of the patient supporting device 200 after the one of the one or more components of the treatment machine 11 is moved.

Figure 10:
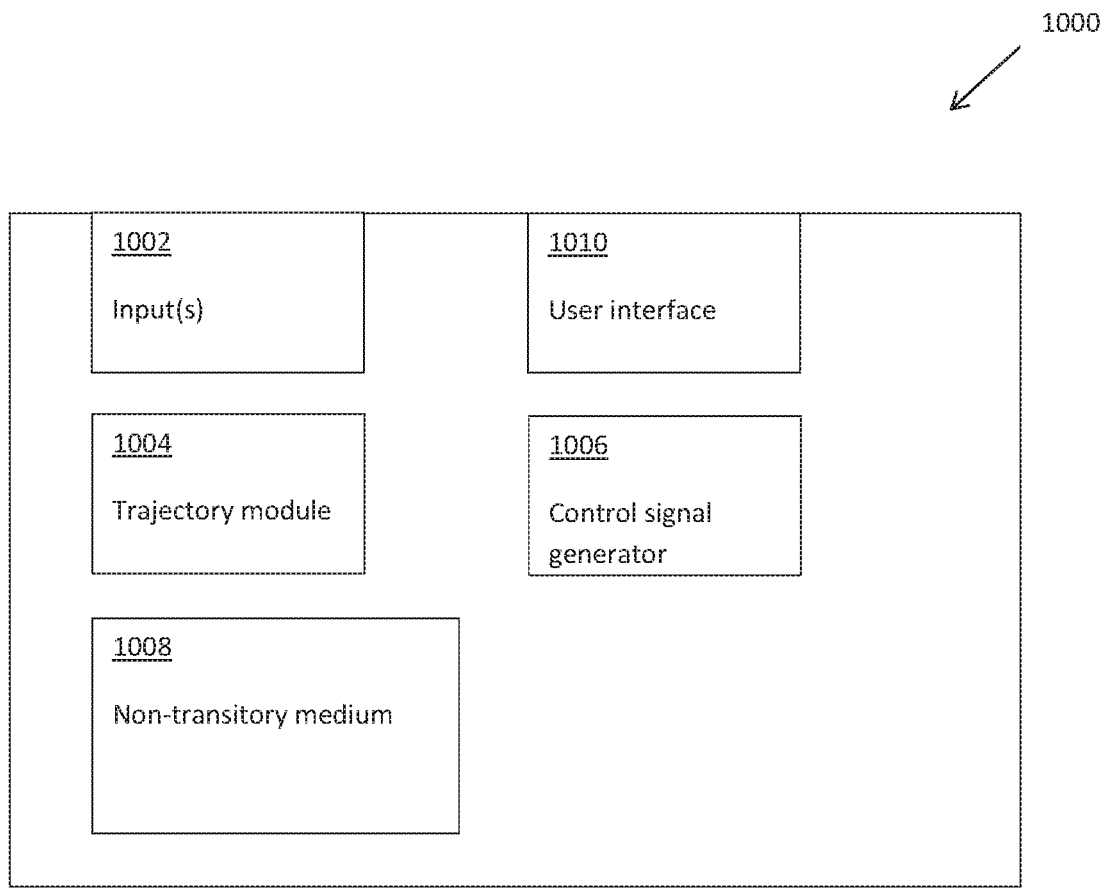
FIG. 10 illustrates an apparatus for controlling a medical system.

FIG. 10 illustrates an apparatus 1000 for controlling a medical system in accordance with some embodiments. The medical system may comprise a treatment machine and a patient supporting device, such as the example shown in FIG. 1. In some embodiments, the apparatus 1000 may be used to perform the method 900 of FIG. 9. Also, in some embodiments, the apparatus 1000 may be a component of the processing unit 54.

Referring to FIG. 10, the apparatus 1000 includes one or more input(s) 1002 for obtaining a current position associated with the patient supporting device 200, and a desired position associated with the patient supporting device 200 to be achieved. In some embodiments, the current position occurs when a treatment is stopped (e.g., interrupted), and the desired position is for unloading the patient 28 from the patient support 14. In other embodiments, the current position is for loading the patient 28 onto the patient support 14, and the desired position is for delivering treatment to the patient 28. The apparatus 1000 also includes a trajectory module 1004 configured to determine trajectories for one or more components of the treatment system 10 (e.g., one or more components of the treatment machine 11, one or more components of the patient supporting device 200, one or more components of an imaging device, or any combination of the foregoing), and an order of the trajectories, based on the current position and the desired position associated with the patient supporting device 200 (e.g., a desired position of the patient support 14). The apparatus 1000 further includes a control signal generator 1006 for outputting one or more control signal(s) to operate the one or more components of the treatment system 10 (e.g., one or more components of the treatment machine 11, one or more components of the patient supporting device 200, one or more components of an imaging device, or any combination of the foregoing) based on the determined trajectories and the order of the trajectories.

In some embodiments, the one or more input(s) may be configured to perform item 902 and/or item 904 of the method 900.

Also, in some embodiments, the trajectory module 1004 may be configured to perform item 906 of the method 900. In some cases, the trajectory module 1004 may be configured to determine the trajectories and the order of the trajectories using a shortest-path algorithm.

In addition, in some embodiments, the control signal generator 1006 may be configured to perform item 908 of the method 900. In some cases, the control signal generator 1006 is configured to output the one or more control signal(s) to move one of the one or more components of the treatment machine 11 to open up a path for the one or more components of the patient supporting device 200, and to move one of the one or more components of the patient supporting device 200 after the one of the one or more components of the treatment machine 11 is moved.

In some embodiments, the apparatus 1000 may also include a non-transitory medium 1008 for storing the current position associated with the patient supporting device 200, the desired position associated with the patient supporting device 200, the trajectories determined by the trajectory module 1004, the order of the trajectories, or any combination of the foregoing. Although the non-transitory medium 1008 is illustrated to be in the apparatus 1000, in other embodiments, the non-transitory medium 1008 may be outside the apparatus 1000 and is communicatively coupled to the apparatus 1000.

Also, in some embodiments, the apparatus 1000 may include a user interface 1010 for receiving one or more input from a user. For example, a user may use the user interface 1010 to enter desired position for the patient support 14. The user may also use the user interface 1010 to input one or more parameters for allowing the apparatus 1000 to perform an optimization to determine trajectories for the one or more components of the treatment system 10 and an order of the trajectories.

In addition, in some embodiments, the user interface 1010 may include one or more control for allowing a user to stop a treatment (e.g., to interrupt a treatment).

After the treatment is stopped, and after the trajectory module 1004 determines the trajectories for the component(s) of the treatment system 10 and the order of the trajectories, the user interface 1010 may then allow a user to enter a command to operate the treatment system 10 so that the determined trajectories may be executed in accordance with the determined order of the trajectories. For example, the user interface 1010 may ask the user whether to move the patient support 14 to a safe loading position. If the user selects a control to indicate that such is desired, the control signal generator 1006 may then execute the trajectories to move the patient support 14 from its initial position when treatment is stopped to a desired position. Thus, the user does not need to specify which component(s) of the treatment system 10 to move, does not need to specify which direction(s) to move the component(s), does not need to specify range(s) of motion(s) for the component(s), and does not need to specify the order of the movements of the components. In other words, the user operation is independent of the direction(s) and range(s) of movement of the component(s).

In the above embodiments, the user interface 1010 allows the user to enter a single command for executing all of the trajectories in the sequence. In other embodiments, the user interface 1010 may allow a user to enter multiple commands for executing the trajectories. For example, assuming that the trajectories and the order of the trajectories are determined by the trajectory module 1004 as follow:

(1) Rotate gantry 12 to the 0° angle, and simultaneously retract an arm of an imaging device.

(2) rotate a first arm of the patient supporting device 200 from position P1 to P2, and simultaneously rotate a second arm of the patient supporting device 200 from position P3 to P4.

(3) lower the patient support 14 to a prescribed elevation. Following the above example, the user interface 1010 may allow a user to enter a first command to execute trajectories (1), a second command to execute trajectories (2), and a third command to execute the trajectory (3). In one implementation, the first command may be a selection of a "proceed" option, which when selected, will cause the apparatus 1000 to operate the treatment system 10 to perform the trajectories (1). After the trajectories (1) above have been performed, the operation of the treatment system 10 to move its components is stopped, and will not continue until the user enters a second command through the user interface 1010. In response to the user entering the second command, the apparatus 1000 then operates the treatment system 10 to perform the trajectories (2) in the above example. After the trajectories (2) above have been performed, the operation of the treatment system 10 to move its component is again stopped, and will not continue until the user enters a third command through the user interface 1010. In response to the user entering the third command, the apparatus 1000 then operates the treatment system 10 to perform the trajectory (3) in the above example. In this example, each of the user commands is independent of the corresponding trajectory/trajectories in the sense that the user command does not specify the direction(s) and range(s) of motion for the trajectory/trajectories. Also, the above feature of allowing a user to approve one or more trajectories before executing them is advantageous because if the user notices that a certain trajectory may be undesirable, the user will have the option of terminating the operation of the treatment system 10.

In the above examples, the trajectories were described with reference to moving the patient support 14 from an initial position where treatment is stopped to a desired position for unloading the patient 28. Alternative, the trajectories may be for moving the patient support 14 from an initial position where the patient 28 is loaded onto the patient support 14 to a desired position where treatment can be delivered to the patient 28.

It should be noted that the automatic movement feature of the patient supporting device 200 is advantageous because it obviates the need for a user to determine which components of the patient supporting device 200 to move, it obviates the need for a user to determine the direction and extent of the movement of the component(s) of the patient supporting device 200, and/or it obviates the need for a user to determine an order of movements for the various components of the patient supporting device 200. The patient supporting device 200 is a technological improvement over existing patient supporting devices because it is believed that existing patient supporting devices do not have the intelligence and processing functions provided in embodiments of the patient supporting device 200.

Specialized Processing System

Figure 12:
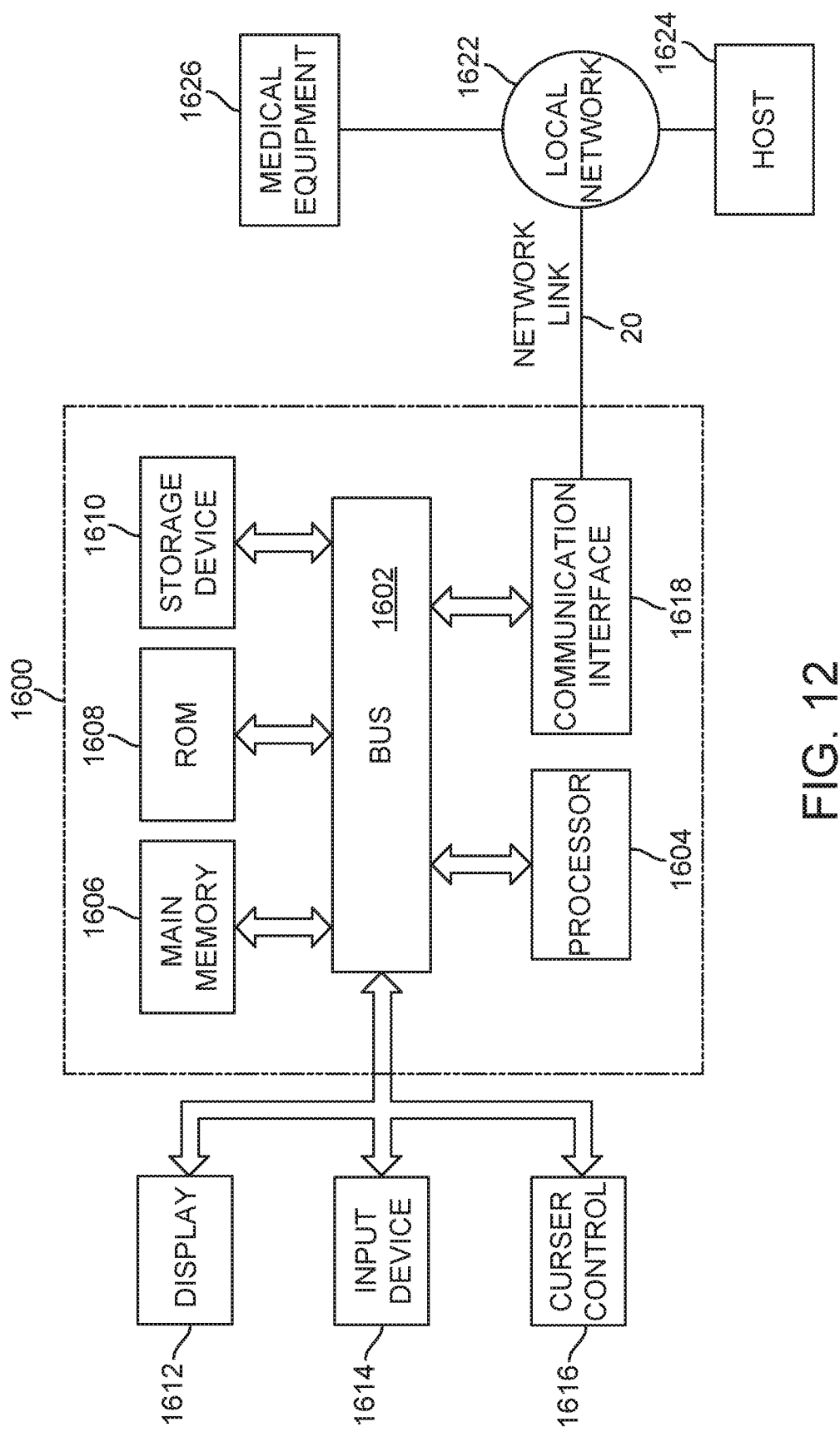
FIG. 12 is a block diagram of a specialized processing system.

FIG. 12 is a block diagram illustrating an embodiment of a specialized processing system 1600 that can be used to implement various embodiments described herein. For example, the processing system 1600 may be configured to operate the patient supporting device 200 in accordance with some embodiments. Also, in some embodiments, the processing system 1600 may be used to implement the control for the patient supporting device 200 and/or the processing unit 54 of FIG. 1. The processing system 1600 may also be an example of the apparatus 800 and/or the apparatus 1000. The processing system 1600 may also be any processor described herein.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. An apparatus for creating a radiation treatment plan for execution by a radiation treatment machine, comprising:
    a waypoint module configured to obtain imaging waypoint data representing imaging waypoints, the imaging waypoints indicating respective temporal opportunities to image a patient during a treatment session, wherein each of the temporal opportunities represents a time point or time slot in which imaging of the patient is possible;
    a treatment trajectory module configured to obtain treatment data at least partially defining a beam-on direction; and
    a treatment plan generator configured to create the radiation treatment plan based at least in part on the imaging waypoint data and the treatment data;
    wherein the apparatus is configured to obtain a user input indicating a desired gantry position, a desired couch position, a desired couch orientation, a desired image energy source position, or any combination of the foregoing, that is associated with one or more of the temporal opportunities for imaging the patient.

2. The apparatus of claim 1, wherein the treatment data defines a gantry angle or a range of gantry angles for an energy source to deliver treatment energies.

3. The apparatus of claim 1, wherein the treatment data defines a couch position, a couch orientation, a treatment energy source position, or any combination of the foregoing, for delivering one or more treatment energies to the patient.

4. The apparatus of claim 1, wherein the treatment trajectory module is also configured to determine a set of possible trajectories.

5. The apparatus of claim 4, wherein the treatment trajectory module is configured to determine the set of possible trajectories based on collision avoidance, imaging capability, or both.

6. The apparatus of claim 4, further comprising a user interface for receiving an input representing a selected one or more of the possible trajectories.

7. An apparatus for creating a radiation treatment plan for execution by a radiation treatment machine, comprising:
    a waypoint module configured to obtain imaging waypoint data representing imaging waypoints, the imaging waypoints at least partially defining one or more positions for obtaining images of a patient during a treatment session;
    a treatment trajectory module configured to obtain treatment data at least partially defining a beam-on direction; and
    a treatment plan generator configured to create the radiation treatment plan based at least in part on the imaging waypoint data and the treatment data;
    wherein the imaging waypoints represented by the imaging waypoint data corresponds with a number of imaging configurations, and wherein the treatment plan generator is configured to create the radiation treatment plan by maintaining the number of the imaging configurations.

8. The apparatus of claim 7, wherein the treatment trajectory module is configured to obtain the treatment data based on the imaging waypoint data.

9. The apparatus of claim 8, wherein the imaging waypoint data comprises a user input indicating a desired position for imaging, wherein the treatment trajectory module is configured to obtain the treatment data based on the user input.

10. An apparatus for creating a radiation treatment plan for execution by a radiation treatment machine, comprising:
    a waypoint module configured to obtain imaging waypoint data representing imaging waypoints, the imaging waypoints indicating respective temporal opportunities to image a patient during a treatment session, wherein each of the temporal opportunities represents a time point or time slot in which imaging of the patient is possible;
    a treatment trajectory module configured to obtain treatment data at least partially defining a beam-on direction; and
    a treatment plan generator configured to create the radiation treatment plan based at least in part on the imaging waypoint data and the treatment data;
    wherein the treatment plan generator is configured to create the radiation treatment plan by prescribing treatment energy to be delivered, and by prescribing imaging be performed during one or more of the temporal opportunities.

11. The apparatus of claim 10, further comprising a direction proposal generator configured to generate proposed directions where imaging is possible based on the treatment data, wherein the waypoint module is configured to obtain the imaging waypoint data based on one or more of the proposed directions.

12. The apparatus of claim 11, further comprising a user interface configured to receive a user input indicating a selected one of the proposed directions, wherein the waypoint module is configured to obtain the imaging waypoint data based on the user input.

13. A method for creating a radiation treatment plan for execution by a radiation treatment machine, comprising:

obtaining imaging waypoint data representing imaging waypoints, wherein the imaging waypoints indicating respective temporal opportunities to image a patient, wherein each of the temporal opportunities represents a time point or time slot in which imaging of the patient is possible;

obtaining treatment data at least partially defining a beam-on direction; and creating the radiation treatment plan based at least in part on the imaging waypoint data and the treatment data;

wherein the method further comprises obtaining a user input indicating a desired gantry position, a desired couch position, a desired couch orientation, a desired image energy source position, or any combination of the foregoing, that is associated with one or more of the temporal opportunities for imaging the patient.

14. The method of claim 13, wherein the treatment data defines a gantry angle or a range of gantry angles for an energy source to deliver treatment energies.

15. The method of claim 13, wherein the treatment data defines a couch position, a couch orientation, a treatment energy source position, or any combination of the foregoing, for delivering one or more treatment energies to the patient.

16. The method of claim 13, further comprising determining a set of possible trajectories.

17. The method of claim 16, wherein the set of possible trajectories is determined based on collision avoidance, imaging capability, or both.

18. The method of claim 16, further comprising receiving an input representing a selected one or more of the possible trajectories.

19. A method for creating a radiation treatment plan for execution by a radiation treatment machine, comprising:

obtaining imaging waypoint data representing imaging waypoints, wherein the imaging waypoints at least partially define one or more positions for obtaining images of a patient;

obtaining treatment data at least partially defining a beam-on direction; and creating the radiation treatment plan based at least in part on the imaging waypoint data and the treatment data;

wherein the imaging waypoints represented by the imaging waypoint data corresponds with a number of imaging configurations, and wherein the act of creating the radiation treatment plan comprises maintaining the number of the imaging configurations.

20. The method of claim 19, wherein the treatment data is obtained based on the imaging waypoint data.

21. The method of claim 20, wherein the imaging waypoint data comprises a user input indicating a desired position for imaging, wherein the treatment data is obtained based on the user input.

22. A method for creating a radiation treatment plan for execution by a radiation treatment machine, comprising:

obtaining imaging waypoint data representing imaging waypoints, wherein the imaging waypoints indicate respective temporal opportunities to image a patient, wherein each of the temporal opportunities represents a time point or time slot in which imaging of the patient is possible;

obtaining treatment data at least partially defining a beam-on direction; and creating the radiation treatment plan based at least in part on the imaging waypoint data and the treatment data;

wherein the created radiation treatment plan prescribes treatment energy to be delivered, and prescribes imaging to be performed during one or more of the temporal opportunities.

23. The method of claim 22, further comprising generating proposed directions where imaging is possible based on the treatment data, wherein the imaging waypoint data is obtained based on the proposed directions.

24. The method of claim 23, further comprising receiving a user input indicating a selected one of the proposed directions, wherein the imaging waypoint data is obtained based on the user input.

* * * * *